(12) United States Patent
Tsuruoka et al.

(10) Patent No.: US 10,053,488 B2
(45) Date of Patent: Aug. 21, 2018

(54) METHOD OF LIBERATING PEPTIDE AND METHOD OF RECOVERING PEPTIDE

(71) Applicant: SYSMEX CORPORATION, Kobe-shi, Hyogo (JP)

(72) Inventors: Rena Tsuruoka, Hyogo (JP); Sanai Tsunokuni, Saitama (JP); Yukiko Miura, Hyogo (JP); Hiroyuki Kabata, Hyogo (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 28 days.

(21) Appl. No.: 15/245,348

(22) Filed: Aug. 24, 2016

(65) Prior Publication Data
US 2017/0057991 A1 Mar. 2, 2017

(30) Foreign Application Priority Data
Aug. 28, 2015 (JP) .................. 2015-169198

(51) Int. Cl.
*A61K 38/00* (2006.01)
*C07K 1/00* (2006.01)
*C07K 1/14* (2006.01)

(52) U.S. Cl.
CPC ................ *C07K 1/14* (2013.01); *C07K 1/145* (2013.01)

(58) Field of Classification Search
CPC .... A61K 9/5089; C07K 14/775; C07K 16/00; C07K 16/2875
See application file for complete search history.

(56) References Cited

U.S. PATENT DOCUMENTS

| 2012/0244634 A1 | 9/2012 | Kabata et al. |
| 2012/0277407 A1 | 11/2012 | Yamamoto et al. |
| 2013/0295689 A1 | 11/2013 | Kabata et al. |
| 2015/0210736 A1 | 7/2015 | Iwai et al. |
| 2016/0033500 A1 | 2/2016 | Miura et al. |

FOREIGN PATENT DOCUMENTS

| EP | 2902407 A1 | 8/2015 |
| EP | 2902408 A1 | 8/2015 |
| WO | 02/48164 A2 | 6/2002 |
| WO | 2004/113275 A2 | 12/2004 |
| WO | 2005/104763 A2 | 11/2005 |

OTHER PUBLICATIONS

Ingles D L: "Preparation of Bisulphite Addition Compounds of 5-Amino-5-Deoxy-$_D$-Xylose", Australian Journal of Chemistry: An International Journal for Chemical Science, C S I R O Publishing, AU, vol. 19, No. 4, Jan. 1, 1966 (Jan. 1, 1966), pp. 667-673, XP000670749, ISSN: 0004-9425 (7 pages).

*Primary Examiner* — Hasan S Ahmed
*Assistant Examiner* — Kaipeen E Yang
(74) *Attorney, Agent, or Firm* — Sughrue Mion, PLLC

(57) ABSTRACT

Disclosed is a method of liberating a peptide, the method comprising a step of bringing a self-aggregate of albumin containing a peptide incorporated therein into contact with a solution that contains a compound represented by Formula (I) or (II) defined in the specification at a concentration of 80 mM to 1000 mM and allowing the peptide to be liberated from the self-aggregate of albumin into the solution.

18 Claims, 10 Drawing Sheets

METHOD OF LIBERATING PEPTIDE AND METHOD OF RECOVERING PEPTIDE

CROSS REFERENCE TO RELATED APPLICATIONS

This application claims priority from prior Japanese Patent Application No. 2015-169198, filed on Aug. 28, 2015, entitled "METHOD OF LIBERATING PEPTIDE, METHOD OF RECOVERING PEPTIDE, PEPTIDE-LIBERATOR, AND REAGENT KIT", the entire contents of which are incorporated herein by reference.

TECHNICAL FIELD

The present invention relates to a method of liberating a peptide incorporated into a self-aggregate of albumin and a method of recovering the peptide.

BACKGROUND

There is a large amount of albumin in blood. It is known that since albumin in blood binds to a peptide in blood to form a complex, albumin interferes with the detection of peptide in blood. Therefore, there is a need to separate albumin from a peptide, namely to liberate a peptide from a complex of albumin and peptide. For example, US Patent Application Publication No. 2012/277407 describes that a liquid sample containing a complex of peptide and albumin undergoes heat treatment, and a self-aggregate of albumin is formed in the liquid sample, so that the peptide is liberated from the complex.

As described in US Patent Application Publication No. 2012/277407, the present inventors have found that a liquid sample containing a complex of peptide and albumin undergoes heat treatment, and a self-aggregate of albumin is formed in the liquid sample, so that the peptide is liberated from the complex (US Patent Application Publication No. 2012/277407 is herein incorporated by reference). It has been considered that the self-aggregate of albumin almost loses the ability to bind to peptides due to denaturation of higher order structure of albumin upon heat treatment. However, the present inventors have found that some of the peptides are not liberated by the heat treatment and are incorporated into the self-aggregate of albumin. Accordingly, there is a demand for the development of a means for liberating a peptide incorporated into a self-aggregate of albumin.

SUMMARY OF THE INVENTION

The scope of the present invention is defined solely by the appended claims, and is not affected to any degree by the statements within this summary.

The present invention provides a method of liberating a peptide. The method comprises bringing a self-aggregate of albumin comprising a peptide incorporated therein into contact with a solution that comprises a compound represented by Formula (I) or (II), a concentration of the compound being 80 mM to 1000 mM in the solution, and allowing the peptide to be liberated from the self-aggregate of albumin into the solution:

[Formula 1]

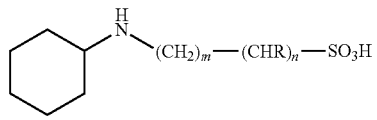

(I)

(wherein m represents an integer of 0 to 4, n represents an integer of 0 to 4, provided that m+n is not less than 4; R is —H or —OH)

or

[Formula 2]

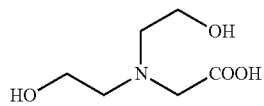

(II)

DETAILED DESCRIPTION OF THE PREFERRED EMBODIMENTS

[1. Method of Liberating Peptide]

Figure 1:
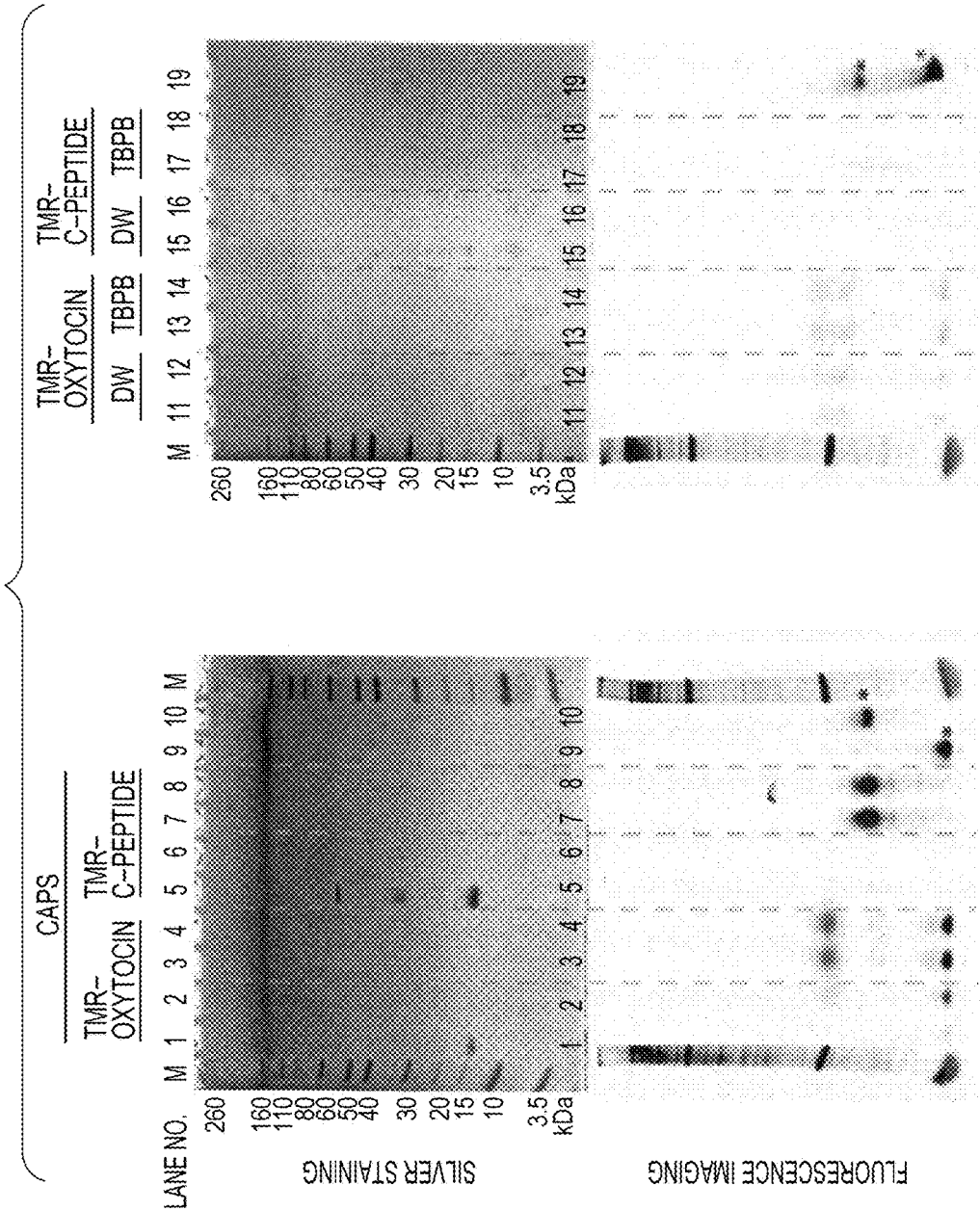
FIG. 1 shows photographs of gels analyzed with fluorescence imaging and silver staining of gels obtained by electrophoresis of samples prepared by homogenizing insoluble fractions with various additives such as CAPS.

A method of liberating a peptide (hereinafter simply referred to as "liberation method") according to the present embodiment allows for liberation of the peptide which is not liberated by heat treatment and is still incorporated into a self-aggregate of albumin formed by heat treatment, among peptides which are bound to albumin to form a complex. Therefore, the liberation method of the present embodiment is a method of liberating a peptide incorporated into a self-aggregate of albumin. All various steps and operations of the liberation method of the present embodiment are performed in vitro.

In the present embodiment, the self-aggregate of albumin is an aggregate of denatured albumin which is formed by heat-treating a liquid sample containing a complex of peptide and albumin. The term "albumin" used herein has the same meaning as the term generally known in the field of biology and is a generic term for a group of soluble proteins contained in animal and plant cells or body fluids. In the present embodiment, the albumin consisting of the "complex of peptide and albumin" is not particularly limited as long as it is an undenatured albumin. Examples of the albumin derived from animals include serum albumin, ovalbumin, and lactalbumin. Examples of the albumin derived from vegetables include leucosin, legumelin, and ricin.

The liquid sample is not particularly limited as long as it contains the complex of peptide and albumin. In the art, it is known that undenatured albumin proteins tend to bind to peptides to form complexes. Therefore, in a case where a peptide or peptides and undenatured albumin coexist in a liquid sample, the liquid sample is thus a target to be subjected to the liberation method of the present embodiment.

The liquid sample may be a biological sample collected from a living body. The biological sample should be a body fluid containing albumin. Examples thereof include blood, plasma, and serum. In a preferred embodiment, the liquid sample is blood, plasma or serum. Blood, plasma or serum diluted with an appropriate solvent may be used as the liquid sample. The solvent is preferably an aqueous solvent. Examples thereof include water, physiological saline, and buffers.

The peptide present in the liquid sample is not particular limited, and it may be a naturally occurring or synthetic peptide. The peptide has preferably a length of 8 to 100 amino acids, more preferably a length of 8 to 60 amino acids, and even more preferably a length of 8 to 40 amino acids. The isoelectric point of the peptide is not particularly limited, and the peptide may be any of a basic peptide, an acidic peptide, and a neutral peptide.

The present inventors have found that a peptide containing a cysteine residue (hereinafter also referred to as "Cys") and an acidic peptide are easily incorporated into a self-aggregate of albumin formed by heat treatment. Consequently, the liberation method of the present embodiment is suitable for liberation of a Cys-containing peptide and an acidic peptide.

In a case where the liquid sample is a biological sample collected from a living body, the peptide liberated from the self-aggregate of albumin may be a peptide present in the biological sample. Examples of the peptide include peptides derived from a living body, which are contained in biological samples collected from a living body, such as blood, plasma, and serum.

The peptide present in the biological sample collected from a living body is preferably a biomarker present in blood. Examples of the peptide include, but are not limited to, oxytocin, C-peptide, insulin, gastrin, glucagon, ghrelin, atrial natriuretic polypeptide (ANP), brain natriuretic peptide (BNP), adrenocorticotropichormone (ACTH), bradykinin, α-endorphin, complement fragments (such as C3f and C4a), ITIH4 fragment, β-amyloid peptide (Aβ), kininogen, fibrinogen, fibrinopeptide, dynorphin, calcitonin, prolactin, and blood coagulation factor XIII (Factor XIII). That is, in the present embodiment, the peptide to be liberated from the self-aggregate of albumin may be one that has an unidentified novel sequence of amino acids.

As described above, the self-aggregate of albumin can be formed by heat-treating a liquid sample containing a complex of peptide and albumin. In the heat treatment, the liquid sample should usually be performed at a temperature of 140° C. to 260° C. inclusive for 5 minutes to 19 hours inclusive. In a case where the heating temperature is 140° C. or more and less than 155° C., the heating time is preferably at least 90 minutes and particularly preferably at least 120 minutes. In a case where the heating temperature is 155° C. or more and less than 170° C., the heating time is preferably at least 20 minutes. In a case where the heating temperature is 170° C. or more, the heating time is preferably at least 5 minutes.

The method of heat treatment is not particularly limited as long as it is a method capable of heating the liquid sample at the temperatures described above. The method is selected from known methods in the art. Examples of the method include a method of external heating by heat conduction and a method of heating by microwaves. The apparatus of heat treatment is not particularly limited as long as it is an apparatus which can heat the liquid sample at controlled temperatures. A hydrothermal reaction vessel and a microwave irradiation device are used, for example.

The liquid sample containing a complex of peptide and albumin is heat-treated to form a supernatant containing a liberated peptide and an insoluble fraction containing a self-aggregate of albumin. In the present embodiment, it is preferable that the supernatant formed by the heat treatment is recovered and the insoluble fraction is left in a container, or the insoluble fraction is recovered and transferred to another container, whereby the self-aggregate of albumin is separated from the supernatant.

In the liberation method of the present embodiment, the peptide incorporated into the self-aggregate of albumin is liberated by bringing the self-aggregate of albumin into contact with a solution that contains a compound represented by Formula (I) or (II) below at a predetermined concentration.

[Formula 3]

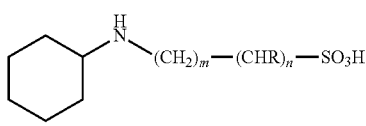

(wherein m represents an integer of 0 to 4, n represents an integer of 0 to 4, provided that m+n is not less than 4; R is —H or —OH)

or

[Formula 4]

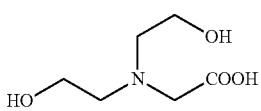

Examples of the compound represented by Formula (I) include 3-(cyclohexylamino)-1-propanesulfonic acid (CAPS), 2-(cyclohexylamino)ethanesulfonic acid (CHES), 3-(cyclohexylamino)-2-hydroxypropanesulfonic acid (CAPSO), 4-(cyclohexylamino)-1-butanesulfonic acid (CABS) and N-cyclohexylsulfamic acid. The structural formulae of these compounds are shown below.

[Formula 5]

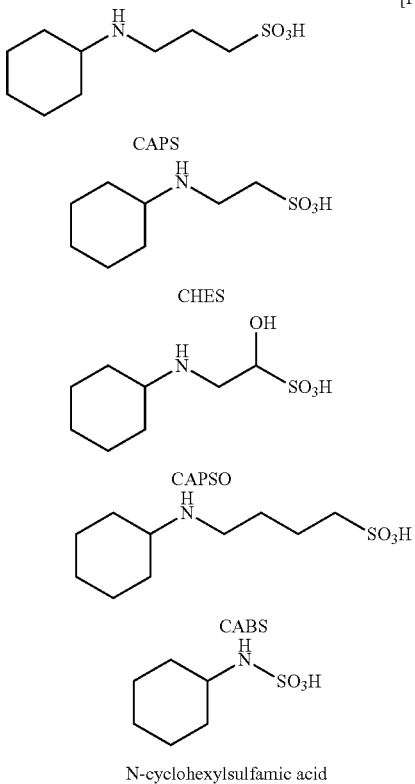

The compound represented by Formula (II) is N,N-di-(2-hydroxyethyl) glycine, and is also called "bicine". These compounds are known in the art and are commonly available.

In the present embodiment, one or two kinds or more of the compounds may be used in combination. Among these compounds, CAPS and CHES are preferred from the viewpoint of the effect of liberating the peptide from the self-aggregate of albumin and the purity of the liberated peptide.

The lower limit of the concentration of the compound represented by Formula (I) or (II) in the solution is usually 80 mM, preferably 100 mM, and more preferably 500 mM. The upper limit of the concentration is usually 1000 mM and preferably 800 mM. When the concentration is 1000 mM or less, a saturated solution of the compound may be used. In respect to CAPS, CHES, CAPSO, and CABS, it is difficult to prepare a solution with a concentration higher than 1000 mM, and thus 1000 mM corresponds to the concentration where these compounds are saturated. Accordingly, the concentration should be usually determined in the range of 80 mM to 1000 mM inclusive. In a case where two or more kinds of compounds are used in combination, the total of the concentrations of the compounds in the solution should be in the above range.

In the present embodiment, a solution containing the compound can be obtained by dissolving the compound in an appropriate solvent so as to have the above concentrations. The solvent is not particularly limited as long as it can dissolve the compound, and it is preferably an aqueous solvent, and more preferably water, physiological saline or a phosphate buffer. Alternatively, the solution containing the compound can be obtained by dissolving the compound in a supernatant of a liquid sample before or after heat treatment so as to have the above concentrations.

The pH of the solution of the compound is not particularly limited and it is preferably an alkaline pH. For example, the pH is from 7.7 to 11.1 inclusive, and more preferably from 8.4 to 10.4 inclusive. The pH of the solution may be adjusted by adding an alkali (NaOH) or acid (HCl).

In a case where the peptide incorporated into the self-aggregate of albumin contains Cys, the peptide may have a chelate bond between Cys and zinc ion. Thus, to the solution of the compound, zinc ion-forming salts such as zinc chloride ($ZnCl_2$) may be added, if necessary. Metal ion-forming salts other than zinc ion-forming salts, which are capable of alternatively forming a chelate bond, may be added. Examples of the metal ion include a copper ion, a cadmium ion, a lead ion, a silver ion, a mercury ion, and a bismuth ion. To the solution of the compound, a reducing agent capable of reducing a disulfide bond may be added. The reducing agent is, for example, dithiothreitol (DTT).

The contact of the solution of the compound with the self-aggregate of albumin can be performed by adding the solution to the self-aggregate of albumin in an appropriate container. At this time, both the solution and the self-aggregate of albumin may be allowed to stand or may be stirred in the contact state. Examples of stirring include homogenization, ultrasonic fragmentation, and aspiration stirring. The contact time is not particularly limited. In the case of leaving the materials to stand, the contact time should be from 1 hour to 72 hours inclusive. In the case of stirring the materials, the contact time should be from 1 minute to 10 minutes inclusive.

The temperature conditions when the solution of the compound is brought into contact with the self-aggregate of albumin are not particularly limited. The temperature of the solution should be such a level that the peptide liberated from the self-aggregate of albumin can be detected. For example, the temperature is from 0° C. to 250° C. inclusive, preferably from 10° C. to 100° C. inclusive, and more preferably from 15° C. to 65° C. inclusive. The ambient temperature during mixing is usually from 15° C. to 37° C. inclusive, and preferably from 20° C. to 28° C. inclusive.

The amount of the solution of the compound is not particularly limited and should be, for example, from the same amount to ten times inclusive of the volume of the self-aggregate of albumin.

In the present embodiment, the solution of the compound is mixed with the self-aggregate of albumin, whereby the peptide incorporated into the self-aggregate is liberated in the solution. The fact that the peptide is liberated in the solution can be confirmed by analysis with any known method in the art. Examples of the method include electrophoresis and mass spectrometry.

[2. Method of Recovering Peptide]

The liberation method of the present embodiment may further include a step of recovering the liberated peptide. That is, the scope of the present disclosure encompasses a method of liberating a peptide incorporated into a self-aggregate of albumin and recovering the peptide (hereinafter, also simply referred to as "recovery method"). Various steps and operations of the recovery method of the present embodiment are performed in vitro.

The scope of the present disclosure encompasses a method comprising, heat-treating a liquid sample containing a complex of peptide and albumin to form a self-aggregate of albumin, so as to allow some of the peptides to be liberated from the complex; recovering a supernatant containing the peptide liberated from the complex; allowing a peptide which is not liberated by the heat treatment and incorporated into the self-aggregate to be liberated; and recovering the supernatant containing the peptide liberated from the self-aggregate. For example, in a case where a sufficient amount of peptide cannot be recovered from the complex of peptide and albumin by the heat treatment, the self-aggregate of albumin formed by the heat treatment is brought into contact with the predetermined solution and the supernatant containing the peptide liberated from the self-aggregate may be recovered. The peptide recovered from the complex of peptide and albumin and the peptide recovered from the self-aggregate are analyzed using a known procedure such as enzyme-linked immunosorbent assay (ELISA), and a specific peptide may be detected from the recovered peptides. A peptide which is the same as some of the peptides liberated from the complex of peptide and albumin may be liberated from the self-aggregate, or a peptide which is different from some of the peptides liberated from the complex of peptide and albumin may be liberated from the self-aggregate.

In the recovery method of the present embodiment, a self-aggregate of albumin containing a peptide is brought into contact with a solution that contains the compound represented by Formula (I) or (II) above at a concentration of 80 mM to 1000 mM inclusive, and the peptide incorporated into the self-aggregate of albumin is allowed to be liberated from the self-aggregate of albumin into the solution.

In the recovery method of the present embodiment, the details of the liquid sample containing the complex of peptide and albumin, the formation of the self-aggregate of albumin, the compound, and the liberation of the peptide incorporated into the self-aggregate of albumin are the same as those described in the liberation method of the present embodiment.

In the recovery method of the present embodiment, the peptide liberated in the solution is recovered. The recovery unit is not particularly limited. For example, the self-aggregate of albumin remains as an insoluble fraction after the contact with the solution of the compound. Thus, only the solution containing the liberated peptide may be recovered by separating the insoluble fraction from the solution of the compound. The insoluble fraction may be separated from the solution of the compound by any known method in the art, such as centrifugation or filtration. The peptide may be purified from the solution containing the liberated peptide by any purification method known in the art.

[3. Peptide-Liberator]

The scope of the present disclosure encompasses a peptide-liberator that is used in the method of liberating a peptide and the method of recovering a peptide (hereinafter also referred to as "liberator"). That is, the liberator of the present embodiment is a liberator for liberating a peptide incorporated into a self-aggregate of albumin.

The liberator of the present embodiment is characterized by containing the compound represented by Formula (I) or (II) above at a concentration of 80 mM to 1000 mM inclusive. The details of the compound are the same as those described in the liberation method of the present embodiment. The lower limit of the concentration of the compound in the peptide-liberator is usually 80 mM, preferably 100 mM, and more preferably 500 mM. The upper limit of the concentration is usually 1000 mM, and preferably 800 mM. Usually, the concentration should be determined in the range of 80 mM to 1000 mM inclusive. In a case where two or more kinds of compounds are contained, the total of the concentrations of the compounds in the liberator should be in the above range.

In the present embodiment, the peptide-liberator is preferably in the form of liquid. In this case, the peptide-liberator can be obtained by dissolving the compound in an appropriate solvent so as to have the above concentration. The solvent is preferably an aqueous solvent and particularly preferably, water, physiological saline, and a phosphate buffer.

Alternatively, the liberator can be prepared by using a reagent kit that includes the compound in the form of a solid such as a powder or crystal and an appropriate solvent for dissolving the compound. In this case, the amount of the compound in the form of a solid and the amount of the solvent should be an amount so that the concentration when the compound is dissolved in the solvent is in the above range.

The liberator may further contain zinc ion-forming salts such as $ZnCl_2$ or metal ion-forming salts which are capable of alternatively forming a chelate bond between Cys and zinc ion. The metal ion is the same as those in the case of the liberation method of the present embodiment. The liberator may further contain a reducing agent capable of reducing a disulfide bond (e.g. DTT).

In a case where the peptide incorporated into the self-aggregate of albumin is liberated using the liberator of the present embodiment, the liberator should be brought into contact with the self-aggregate of albumin. The details of the contact are the same as those described in the liberation method of the present embodiment.

Figure 10:
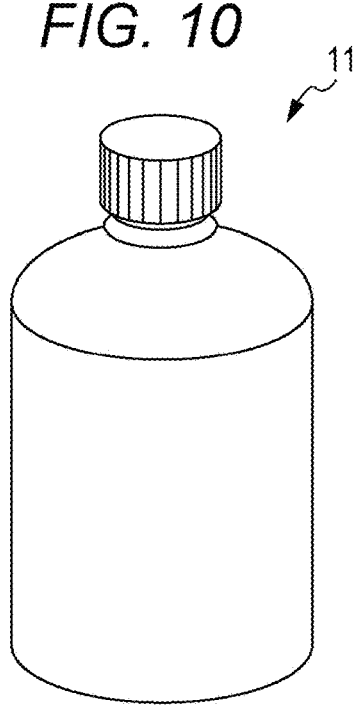
FIG. 10 is a schematic view showing an example of a peptide-liberator of the present embodiment.

FIG. 10 shows an example of the appearance of the liberator of the present embodiment. In the figure, reference numeral 11 denotes a container accommodating the liberator in the form of solution. The container accommodating the liberator of the present embodiment may be accommodated in a box and provided for a user. Package inserts indicating the method of using the liberator, a micro pestle for homogenizing the self-aggregate of albumin, and the like may be enclosed in this box.

The scope of the present disclosure encompasses use of a peptide-liberator that liberates a peptide incorporated into a self-aggregate of albumin, the peptide-liberator containing a compound represented by Formula (I) or (II) below at a concentration of 80 mM to 1000 mM inclusive.

[Formula 6]

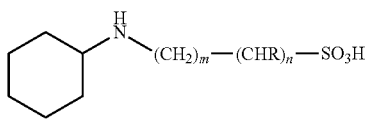

(I)

(wherein m represents an integer of 0 to 4, n represents an integer of 0 to 4, provided that m+n is not less than 4; R is —H or —OH)
or

[Formula 7]

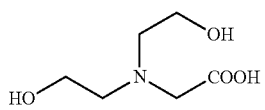

(II)

[4. Reagent Kit]

The scope of the present disclosure encompasses a kit for preparing a peptide-liberator for liberation of a peptide incorporated into a self-aggregate of albumin (hereinafter also referred to as "reagent kit").

The reagent kit of the present embodiment includes a compound represented by Formula (I) or (II) above and a solvent to dissolve the compound. The compound is preferably in the form of a solid such as a powder or crystal. The details of the compound represented by Formula (I) or (II) and the solvent to dissolve the compound are the same as those described in the liberation method of the present embodiment.

In the reagent kit of the present embodiment, the peptide-liberator is characterized by being prepared such that when the compound is mixed with the solvent, the compound has a concentration of 80 mM to 100 mM inclusive. The lower limit of the concentration of the compound in the peptide-liberator to be prepared is usually 80 mM, preferably 100 mM, and more preferably 500 mM. The upper limit of the concentration is usually 1000 mM, and preferably 800 mM. Usually, the concentration should be determined in the range of 80 mM to 1000 mM inclusive. In a case where two or more kinds of compounds are contained, the total of the concentrations of the compounds in the peptide-liberator should be in the above range.

The amount of the compound in the form of a solid and the amount of the solvent are not particularly limited. The compound in the form of a solid and the solvent may be included in the reagent kit such that the concentration when the compound is dissolved in the solvent is in the above range.

Figure 11:
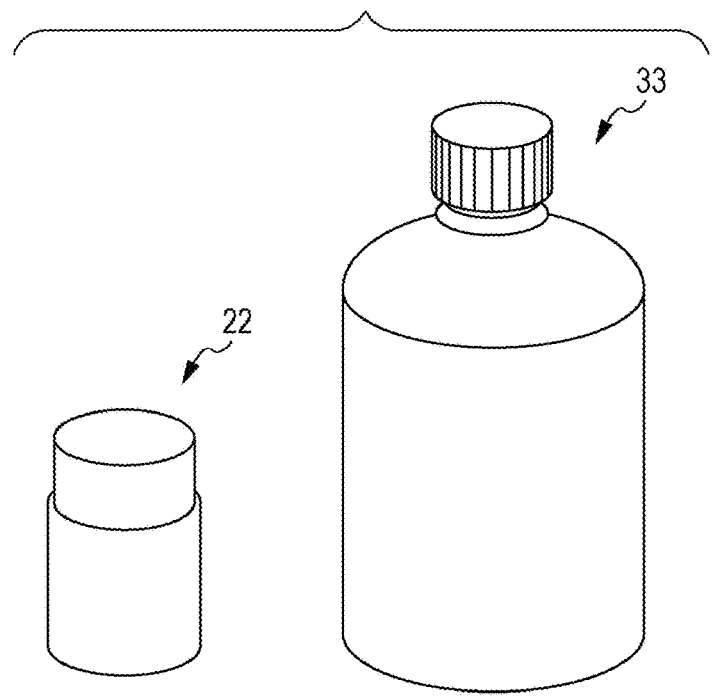
FIG. 11 is a schematic view showing an example of a reagent kit of the present embodiment.

In the reagent kit of the present embodiment, it is preferable that the compound and the solvent are respectively accommodated in different containers or separately packed. FIG. 11 shows an example of the appearance of the reagent kit of the present embodiment. In the figure, reference numeral 22 denotes a container that accommodates the compound represented by Formula (I) or (II), and reference numeral 33 denotes a container accommodating the solvent for dissolving the compound. These containers may be accommodated in a box and provided for a user. Package inserts indicating the method of preparing the liberator, a micro pestle for homogenizing the self-aggregate of albumin, and the like may be enclosed in this box.

The reagent kit may further include zinc ion-forming salts such as $ZnCl_2$ or metal ion-forming salts which are capable of alternatively forming a chelate bond between Cys and zinc ion. The metal ion is the same as those in the case of the liberation method of the present embodiment. The metal salt may be included in the container accommodating the compound represented by Formula (I) or (II) or may be included in the container accommodating the solvent. Alternatively, the metal salt may be accommodated in a container different from the container accommodating the compound and the container accommodating the solvent or may be packed separately from those containers.

The reagent kit further may further include a reducing agent capable of reducing a disulfide bond (e.g. DTT). The reducing agent may be included in the container accommodating the compound represented by Formula (I) or (II) or may be included in the container accommodating the solvent. Alternatively, the reducing agent may be accommodated in a container different from the container accommodating the compound and the container accommodating the solvent or may be packed separately from those containers.

The scope of the present disclosure encompasses use of a reagent kit for preparing a peptide-liberator which liberates a peptide incorporated into a self-aggregate of albumin, the reagent kit including a compound represented by Formula (I) or (II) below and a solvent for dissolving the compound, wherein when the compound is mixed with the solvent, the peptide-liberator is prepared so as to have a concentration of the compound of 80 mM to 1000 mM inclusive.

[Formula 8]

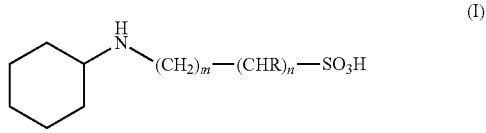

(I)

(wherein m represents an integer of 0 to 4, n represents an integer of 0 to 4, provided that m+n is not less than 4; R is —H or —OH)
or

[Formula 9]

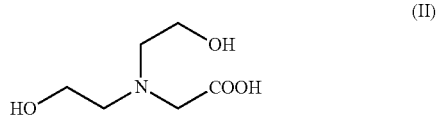

(II)

Hereinafter, the present invention will be described in detail with reference to examples, however the present invention is not limited to the examples.

EXAMPLES

Example 1

Liberation and Recovery of Peptides from Self-aggregate of Albumin

In Example 1, a compound was searched which is usable as a peptide-liberator for liberation of a peptide incorporated into a self-aggregate of albumin. Specifically, it was examined whether it was possible to liberate and recover the peptide incorporated into the self-aggregate of albumin by using additives containing various compounds. As the peptide easily incorporated into the self-aggregate of albumin, two types of acidic peptides were used.

(1.1) Materials
Additives

Additives used were a 100 mM CAPS aqueous solution (pH 11.0), ultrapure water (18 MΩ·cm) (hereinafter also referred to as "DW"), and a Tris-phosphoric acid buffer (hereinafter also referred to as "TBPB"). The CAPS aqueous solution was obtained by dissolving CAPS (product No. 343-00484: manufactured by DOJINDO LABORATORIES) in water so as to have a final concentration of 100 mM, and adjusting the pH to 11.0 using NaOH. The DW was prepared by ELGA PURELAB ultra (manufactured by ORGANO). The composition of TBPB is as follows: Tris-HCl (pH 7.0, final concentration: 100 mM); sodium phosphate (final concentration: 0.4 mM); and NaCl (final concentration: 6 mM). To each of the CAPS aqueous solution, DW, and TBPB, dithiothreitol (DTT) was added so as to have a final concentration of 0.1 mM, and a DTT-containing additive was prepared.

Peptide

Peptides used were oxytocin as an acidic peptide, TMR-oxytocin obtained by fluorescently labeling C-peptide with tetramethyl rhodamine (TMR) (pI=5.51, two Cys residues: SCRUM), and TMR-C-peptide (pI=3.45, no Cys residue: Biologica). The amino acid sequences of oxytocin and C-peptide are as follows:

Oxytocin: CYIQNCPLG (SEQ ID NO: 1)
C-peptide: EAEDLQVGQVELGGGPGAGSLQPLALEGSLQ (SEQ ID NO: 2)

Liquid Sample

Whole blood (0.3 ml) derived from healthy individuals (purchased from ProMedDx) was 5-fold diluted with a CAPS aqueous solution (pH 11.0). To the resultant diluent, TMR-oxytocin or TMR-C-peptide was added so as to have a final concentration of 2 μM, and a liquid sample containing a complex of peptide and protein (albumin) in blood was prepared.

(1.2) Formation of Self-aggregate of Albumin

To the liquid sample containing a complex of peptide and protein (albumin) in blood, $ZnCl_2$ (NACALAI TESQUE, INC.) was added so as to have a final concentration of 100 mM. A part of the resultant mixture was recovered and stored as a control sample. The remaining mixture was transferred into a 10-mL volume glass tube. The tube was sealed with a Teflon (registered trademark) pressure resistant sealing holder for test tube (Milestone General) and placed in a microwave applicator (MultiSYNTH type, Milestone General). Then, heat treatment was performed by increasing the temperature from room temperature (25° C.) to 100° C. for 30 seconds and then increasing the temperature from 100° C. to 160° C. for 1 minute. Cooling after heating was performed by blowing compressed air to the pressure resistant sealing holder from an air compressor (YC-3 R type, YAEZAKI KUATU. CO., LTD.) connected to the microwave applicator. An insoluble fraction containing a self-aggregate of albumin (hereinafter, simply referred to as "insoluble fraction") was formed in the liquid sample after heat treatment.

(1.3) Liberation and Recovery of Peptides from Self-aggregate of Albumin

The supernatants recovered from the liquid samples after heat treatment were stored as control samples. The insoluble fraction was transferred into a 2-mL volume microtube (manufactured by Eppendorf) using a spatula. A hundred (100) mM CAPS aqueous solution, ultrapure water or TBPB was added to the microtube, and the insoluble fraction was homogenized using a micro pestle for 1 minute. The homogenized insoluble fraction was subjected to centrifugation at 15,000 rpm for 5 minutes and supernatants were obtained. The obtained supernatants were stored as samples.

(1.4) Detection of Peptide

The samples were subjected to SDS-PAGE, followed by fluorescent imaging and silver staining. The specific operation is as below. First, a 60% (w/w) glycerol solution was mixed with each of the samples. Then, electrophoresis was performed on each of the resultant mixtures at 200 V (constant voltage) for 30 minutes using NuPAGE 4-12% Bis-Tris Gel and NuPAGE MES SDS Running Buffer (both are manufactured by Life Technologies Japan). The electrophoresis tank used was X-Cell Sure Lock Minicell (Life Technologies Japan) and the electric power unit used was Power Station 1000XP (ATTO). As for the gel after electrophoresis, TMR-oxytocin and TMR-C-peptide were detected using a fluorescence imager (Pharos FX Molecular Imager type, Bio-Rad Laboratories). Then, the gels taken out from the fluorescence imager were subjected to silver staining using an EZ Stain Silver (product No. AE-1360, manufactured by ATTO), and the contaminating proteins in the samples were detected. The results are shown in FIG. 1.

(1.5) Results

In the photographs of the gels shown in FIG. 1, the samples applied to the Lane Nos. are as follows: The mark "M" indicates a Lane No. in which a size marker was applied.

Lane No. 1: supernatant obtained by centrifuging a liquid sample containing a complex of TMR-oxytocin and albumin which was not heat-treated.

Lane No. 2: supernatant obtained by heat-treating a liquid sample containing a complex of TMR-oxytocin and albumin.

Lane No. 3: supernatant obtained by bringing a self-aggregate of albumin containing TMR-oxytocin incorporated therein into contact with a CAPS aqueous solution and homogenizing the resulting mixture.

Lane No. 4: supernatant obtained by bringing a self-aggregate of albumin containing TMR-oxytocin incorporated therein into contact with a DTT-containing CAPS aqueous solution and homogenizing the resulting mixture.

Lane No. 5: supernatant obtained by centrifuging a liquid sample containing a complex of TMR-C-peptide and albumin which was not heat-treated.

Lane No. 6: supernatant obtained by heat-treating a liquid sample containing a complex of TMR-C-peptide and albumin.

Lane No. 7: supernatant obtained by bringing a self-aggregate of albumin containing TMR-C-peptide incorporated therein into contact with a CAPS aqueous solution and homogenizing the resulting mixture.

Lane No. 8: supernatant obtained by bringing a self-aggregate of albumin containing TMR-C-peptide incorporated therein into contact with a DTT-containing CAPS aqueous solution and homogenizing the resulting mixture.

Lane No. 9: TMR-oxytocin preparation.

Lane No. 10: TMR-C-peptide preparation.

Lane No. 11: supernatant obtained by bringing a self-aggregate of albumin containing TMR-oxytocin incorporated therein into contact with DW and homogenizing the resulting mixture.

Lane No. 12: supernatant obtained by bringing a self-aggregate of albumin containing TMR-oxytocin incorporated therein into contact with DTT containing DW and homogenizing the resulting mixture.

Lane No. 13: supernatant obtained by bringing a self-aggregate of albumin containing TMR-oxytocin incorporated therein into contact with TBPB and homogenizing the resulting mixture.

Lane No. 14: supernatant obtained by bringing a self-aggregate of albumin containing TMR-oxytocin incorporated therein into contact with DTT containing TBPB and homogenizing the resulting mixture.

Lane No. 15: supernatant obtained by bringing a self-aggregate of albumin containing TMR-C-peptide incorporated therein into contact with DW and homogenizing the resulting mixture.

Lane No. 16: supernatant obtained by bringing a self-aggregate of albumin containing TMR-C-peptide incorporated therein into contact with DTT containing DW and homogenizing the resulting mixture.

Lane No. 17: supernatant obtained by bringing a self-aggregate of albumin containing TMR-C-peptide incorporated therein into contact with TBPB and homogenizing the resulting mixture.

Lane No. 18: supernatant obtained by bringing a self-aggregate of albumin containing TMR-C-peptide incorporated therein into contact with DTT containing TBPB and homogenizing the resulting mixture.

Lane No. 19: mixture of TMR-oxytocin preparation and TMR-C-peptide preparation.

In FIG. 1, the bands of Lane Nos. 9 and 10 of the fluorescence imaged gels (indicated by *) represent a band of TMR-oxytocin and a band of TMR-C-peptide, respectively. Two bands of Lane No. 19 of the fluorescence imaged gels (indicated by *) represent a band of TMR-oxytocin and a band of TMR-C-peptide, respectively. In FIG. 1, the photographs of the fluorescence imaged gels show the presence and amount of TMR-labeled peptide, and thus the recovery rate of the obtained peptide can be evaluated. The photographs of the silver-stained gels show the presence and amount of foreign substances in each sample, and thus the purity of the obtained peptide can be evaluated.

Referring to FIG. 1, the TMR-oxytocin was hardly observed in Lane 1 of the fluorescence-imaged gel. This result shows that no TMR-oxytocin was liberated in the non-heat treated liquid sample. In Lane No. 2, a small amount of TMR-oxytocin was confirmed by fluorescence imaging. This result shows that the TMR-oxytocin captured by the protein in blood such as albumin was slightly liberated in the supernatant by the heat treatment. In Lane No. 3, the TMR-oxytocin was confirmed by fluorescence imaging. This result showed that the insoluble fraction formed by the heat treatment of the liquid sample was brought into contact with the CAPS aqueous solution, followed by homogenization, whereby the TMR-oxytocin incorporated in the self-aggregate of albumin was liberated in the CAPS aqueous solution. Hence, it was found that the CAPS aqueous solution can be used as the peptide-liberator for liberation of the peptide incorporated into the self-aggregate of albumin.

A band having a molecular weight higher than that of the TMR-oxytocin was observed in Lane 3. The band is assumed to be a band of the TMR-oxytocin multimer formed from Cys residues in the oxytocin peptide. On the other hand, foreign substances were not observed in Lane 3 of the silver-stained gel, and this indicates that the TMR-oxytocin was selectively liberated. The same result as that of Lane 3 was observed in Lane 4, and this indicates that DTT as the reducing agent may be added to the CAPS aqueous solution as the liberator.

Referring to FIG. 1, the TMR-C-peptide was hardly observed in Lanes 5 and 6 of the fluorescence-imaged gels. This result shows that no TMR-C-peptide was liberated in the non-heat treated liquid sample, and the TMR-C-peptide captured by the protein in blood such as albumin was hardly liberated by the heat treatment of the liquid sample. In Lane 7, the TMR-C-peptide was confirmed by fluorescence imaging. Accordingly, this result showed that the insoluble fraction formed by the heat treatment of the liquid sample was brought into contact with the CAPS aqueous solution, followed by homogenization, whereby the TMR-C-peptide incorporated into the self-aggregate of albumin was liberated in the CAPS aqueous solution. On the other hand, foreign substances were not observed in Lane 7 of the silver-stained gel, and this indicates that the TMR-C-peptide was selectively liberated. The same result as that of Lane 7 was observed in Lane 8 to which the sample treated with the DTT-containing CAPS aqueous solution was applied.

Referring to FIG. 1, as shown in Lanes 11 to 14 of the fluorescence-imaged gels, the insoluble fraction was brought into contact with the DW or TBPB, followed by homogenization, whereby the TMR-oxytocin incorporated into the self-aggregate of albumin was only slightly extracted. As shown in Lanes 15 to 18, even when the insoluble fraction was brought into contact with the DW or TBPB, followed by homogenization, the TMR-C-peptide incorporated into the self-aggregate of albumin could not be extracted. This result showed that the DW and TBPB are not suitable for liberation of the peptide incorporated into the self-aggregate of albumin.

Example 2

Concentration of Liberator (CAPS)

In Example 2, it was examined whether it was possible to liberate and recover a peptide incorporated into a self-aggregate of albumin by using additives containing CAPS with various concentrations. An appropriate CAPS concentration range as a peptide-liberator was determined.

(2.1) Materials

Additives

The additives used were CAPS aqueous solutions (pH 11.0) with CAPS concentrations of 0.1, 1, 10, 20, 50, 80, 100, 500, and 1000 mM. These CAPS aqueous solutions were obtained by dissolving 3-(cyclohexylamino)-1-propanesulfonic acid (product No. 343-00484: manufactured by DOJINDO LABORATORIES) in water so as to have the above concentrations and adjusting the pH to 11.0 using NaOH. To each of the CAPS aqueous solutions, DTT was added so as to have a final concentration of 0.1 mM, and a DTT-containing CAPS aqueous solution (pH 11.0) was also prepared. A 100 mM CAPS aqueous solution (pH 5.7) was prepared.

Peptide

The peptide used was TMR-SA21 in which synthetic peptide SA21 was labeled with TMR (Biologics). SA21 is an acidic peptide (pI=4.11) which has two Cys residues in its amino acid sequence. It is known that SA21 binds to albumin with the highest degree of affinity to form a strong and stable complex (refer to US Patent Application Publication No. 2012/277407). The amino acid sequence of SA21 is DDEWLCGWRPLCIDEILR (SEQ ID NO: 3).

Liquid Sample

Whole blood (0.3 ml) derived from healthy individuals (purchased from ProMedDx) was 5-fold diluted with a CAPS aqueous solution (pH 11.0). To the resultant diluent, TMR-SA21 was added so as to have a final concentration of 2 μM, and a liquid sample containing a complex of peptide and protein (albumin) in blood was prepared.

(2.2) Formation of Self-aggregate of Albumin

To the liquid sample containing a complex of peptide and protein (albumin) in blood, $ZnCl_2$ (NACALAI TESQUE, INC.) was added so as to have a final concentration of 100 mM. The resultant mixture was transferred into a 10-mL volume glass test tube, and the mixture was heat-treated and cooled in the same manner as in Example 1. An insoluble fraction (i.e., the self-aggregate of albumin) was formed in the liquid sample after heat treatment.

(2.3) Liberation and Recovery of Peptides from Self-aggregate of Albumin

The insoluble fraction was transferred from each of the liquid samples after heat treatment into a 2-mL volume microtube (manufactured by Eppendorf) using a spatula. The CAPS aqueous solution was added to the microtube, and the insoluble fraction was homogenized using a micro pestle for 1 minute. The homogenized insoluble fraction was subjected to centrifugation at 15,000 rpm for 5 minutes and supernatants were obtained. The obtained supernatants were stored as samples.

(2.4) Detection of Peptide

Figure 2:
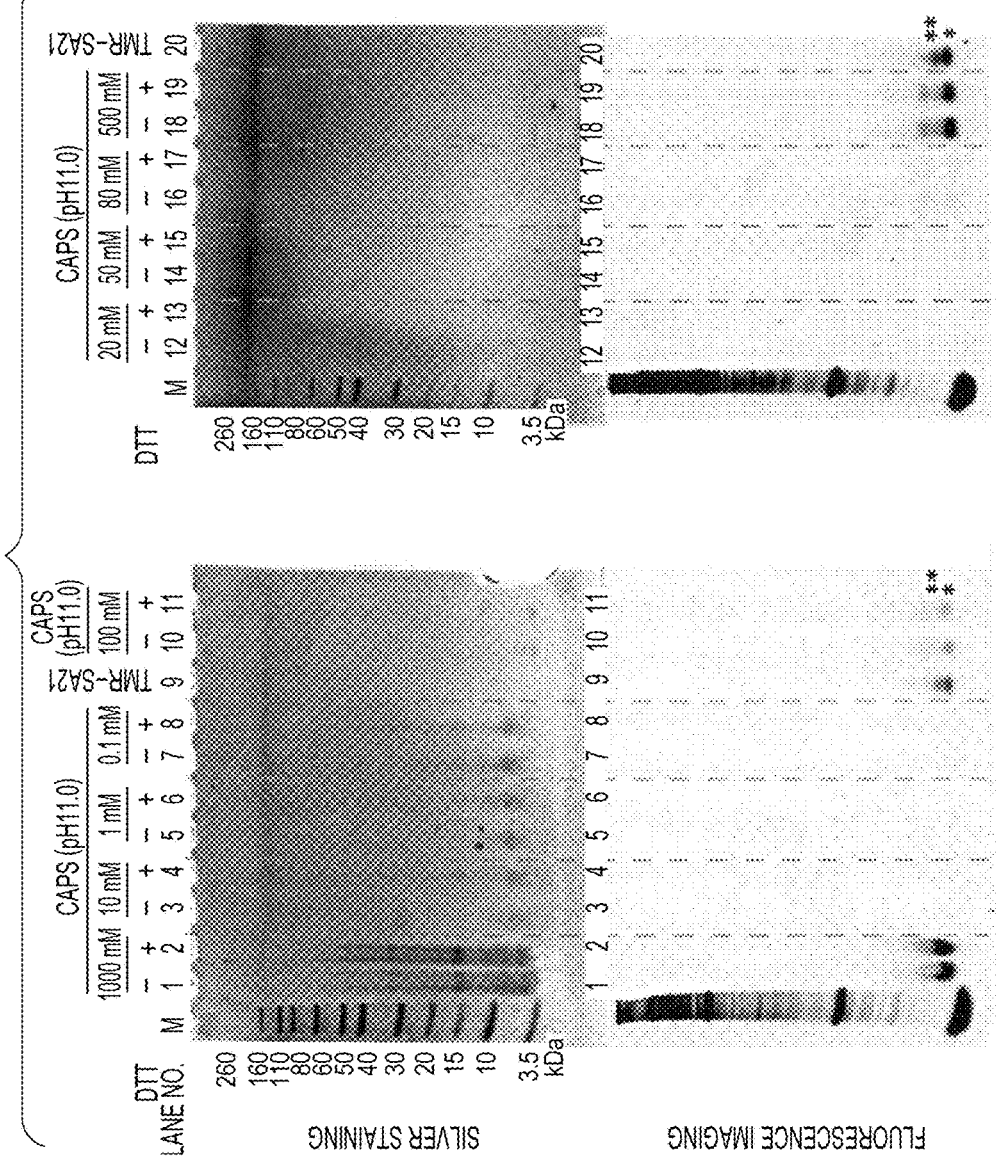
FIG. 2 shows photographs of gels analyzed with fluorescence imaging and silver staining of gels obtained by electrophoresis of samples prepared by homogenizing insoluble fractions with different concentrations of additives (CAPS)
Figure 3:
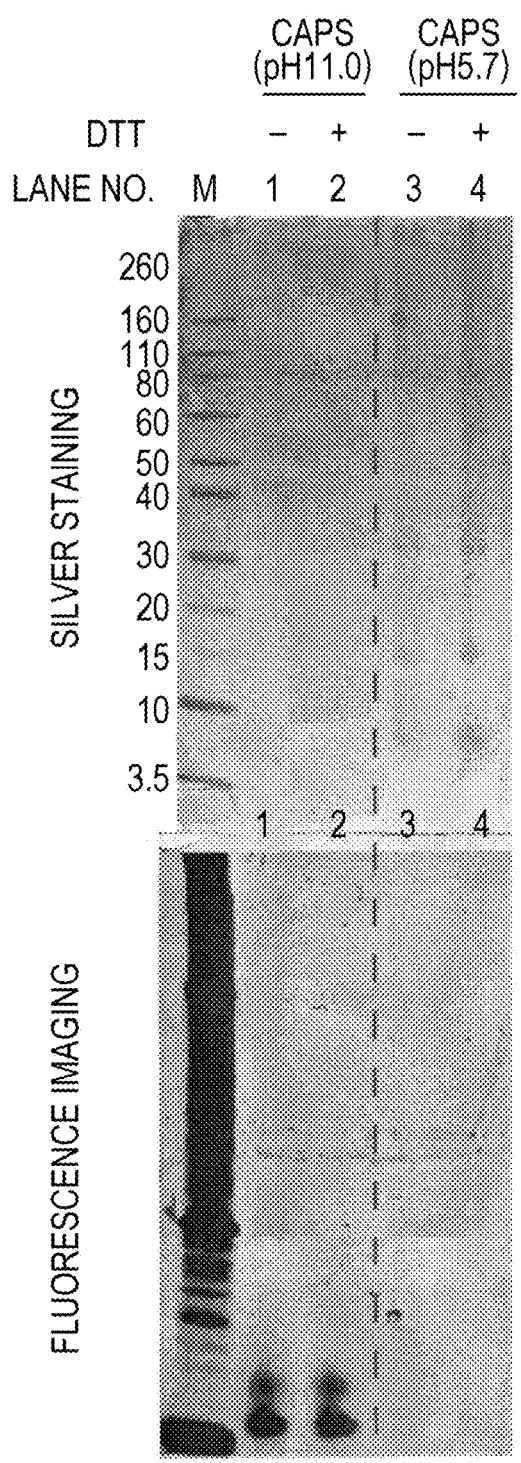
FIG. 3 shows photographs of gels analyzed with fluorescence imaging and silver staining of gels obtained by electrophoresis of samples prepared by homogenizing insoluble fractions with different pHs of additives (CAPS)

The samples were subjected to SDS-PAGE in the same manner as in Example 1, followed by fluorescent imaging and silver staining. FIGS. 2 and 3 show the results analyzed by fluorescence imaging and silver staining of gels after electrophoresis. In FIG. 2, the bands of Lane Nos. 11 and 20 of the fluorescence imaged gels (indicated by *) represent bands of TMR-SA21 monomers and the bands (indicated by **) represent bands of TMR-SA21 multimers.

In fluorescence imaging, TMR-SA21 as for lanes and bands in gels were quantified using a fluorescence imager. Based on the results of fluorescence imaging, the optical shade density (hereinafter referred to as "densitometry value") of the peptide or protein residue was calculated using image processing software ImageJ 1.46r (National Institute of Health), and the relative value of recovery rate (Y) was calculated according to Equation 1 below. At this time, the densitometry value was calculated using a slit width of W (width)=1.0 and H (height)=2.6.

Relative value of recovery rate $(Y)=[(S3/W3)-(S1/W1)]/[(S2/W2)-(S1/W1)]$  Equation 1 wherein, S1 represents a densitometry value of background,
S2 represents a densitometry value of TMR-SA21 preparation,
S3 represents a densitometry value of the lane of interest,
W1 represents a slit width during the densitometry quantification of the background,
W2 represents a slit width during the densitometry quantification of the TMR-SA21 preparation, and
W3 represents a slit width during the densitometry quantification of the lane of interest.

Subsequently, as for the silver-stained gels, the densitometry value of the peptide or protein residue was calculated using image processing software ImageJ 1.46r (NIH), and the relative value of relative amount of impurities (D) was calculated according to Equation 2 below. At this time, a densitogram was formed using a slit width of W (width)=1.0 and H (height)=2.6, similarly to the calculation of the recovery rate. In the obtained densitogram, the densitometry value between the peaks 10 kDa and 60 kDa of the size marker (Sharp Pre-stained Protein Standard: manufactured by Novex) was determined.

Relative value of relative amount of impurities $(D)=$
$[(S3/W3)-(S1/W1)]/[(S2/W2)-(S1/W1)]$  Equation 2 wherein, S1 represents a densitometry value of background,
S2 represents a densitometry value of marker,
S3 represents a densitometry value of the lane of interest,
W1 represents a slit width during the densitometry quantification of the background,
W2 represents a slit width during the densitometry quantification of the marker, and
W3 represents a slit width during the densitometry quantification of the lane of interest.

Based on the calculated relative value of recovery rate and the relative value of relative amount of impurities, the recovery efficiency of peptide was calculated according to Equation 3 below.

Recovery efficiency=relative value of recovery rate $(Y)$/relative value of relative amount of impurities $(D)$  Equation 3

The calculated relative value of recovery rate (Y), relative value of relative amount of impurities (D), and value of recovery efficiency are shown in Table 1.

TABLE 1

| Additive | Concentration (mM) | Relative value of recovery rate (Y) | Relative value of relative amount of impurities (D) | Recovery efficiency (Y/D) |
|---|---|---|---|---|
| CAPS (pH 11.0) | 0.1 | 0 | 0.43 | 0 |
| CAPS (pH 11.0) | 1 | 0 | 0.46 | 0 |
| CAPS (pH 11.0) | 10 | 0 | 0.35 | 0 |
| CAPS (pH 11.0) | 20 | 0 | 0.60 | 0 |
| CAPS (pH 11.0) | 50 | 0 | 0.04 | 0 |
| CAPS (pH 11.0) | 80 | 0.04 | 0.04 | 1.04 |
| CAPS (pH 11.0) | 100 | 0.89 ± 0.76 | 0.17 ± 0.14 | 6.54 ± 4.00 |
| CAPS (pH 11.0) | 500 | 0.90 | 0.04 | 25.64 |
| CAPS (pH 11.0) | 1000 | 1.66 | 0.80 | 2.08 |

(2.5) Results

As shown in FIG. 2 and Table 1, in a case where the CAPS concentration was in the range of 0.1 mM to 50 mM, the SA21 peptide was not liberated from the insoluble fraction. As shown in FIG. 2, in a case where the CAPS concentration was in the range of 0.1 mM to 50 mM, even further addition of DTT as the reducing agent to the additive caused no liberation of the SA21 peptide from the insoluble fraction. On the other hand, in a case where the CAPS concentration was in the range of 80 mM to 1000 mM, the SA21 peptide could be liberated from the insoluble fraction. On the other hand, since foreign substances were hardly liberated, the purity of the recovered SA21 peptide is assumed to be high. Therefore, it was suggested that the range of appropriate CAPS concentration range as the peptide-liberator is from 80 mM to 1000 mM. As shown in FIG. 2, in a case where the CAPS concentration was from 80 mM to 1000 mM, even further addition of DTT to the additive allowed the SA21 peptide to be liberated and recovered from the insoluble fraction. On the other hand, as shown in FIG. 3, when the pH of the CAPS aqueous solution was 5.7, the SA21 peptide could be hardly liberated from the insoluble fraction even if the CAPS concentration was 100 mM. It was suggested that in a case where the pH is lower than neutral, the peptide recovery efficiency decreases.

Example 3

Liberation and Recovery of Peptides with CHES

It was examined whether it was possible to liberate and recover a peptide incorporated into a self-aggregate of albumin by using additives containing CHES (having a structure similar to that of CAPS) with various concentrations. An appropriate CHES concentration range as a peptide-liberator was determined.

(3.1) Materials
Additives

The additives used were CHES aqueous solutions (pH 10.0) with CHES concentrations of 0.1, 1, 10, 50, 80, 100, 500, and 1000 mM. These CHES aqueous solutions were obtained by dissolving 2-(cyclohexylamino) ethane sulfonic acid (product No. 340-08331: manufactured by DOJINDO LABORATORIES) in water so as to have the above concentrations and adjusting the pH to 10.0 using NaOH. To each of the CHES aqueous solutions, DTT was added so as to have a final concentration of 0.1 mM, and a DTT-containing CHES aqueous solution (pH 10.0) was also prepared.

Peptide

The peptide used was the same TMR-SA21 (Biologica) as in Example 2.

Liquid Sample

To diluents of whole blood from healthy individuals, TMR-SA21 was added so as to have a final concentration of 2 μM in the same manner as in Example 2, and liquid samples were prepared.

(3.2) Formation of Self-aggregate of Albumin as Well as Liberation and Recovery of Peptides Each of the liquid samples was heat-treated and cooled in the same manner as in Example 2 to form an insoluble fraction (i.e., a self-aggregate of albumin) in each of the liquid samples. Then, the insoluble fraction was homogenized in the same manner as in Example 2 except that the CHES aqueous solution was used as an additive, and supernatants were obtained. The obtained supernatants were stored as samples.

(3.3) Detection of Peptide

Figure 4:
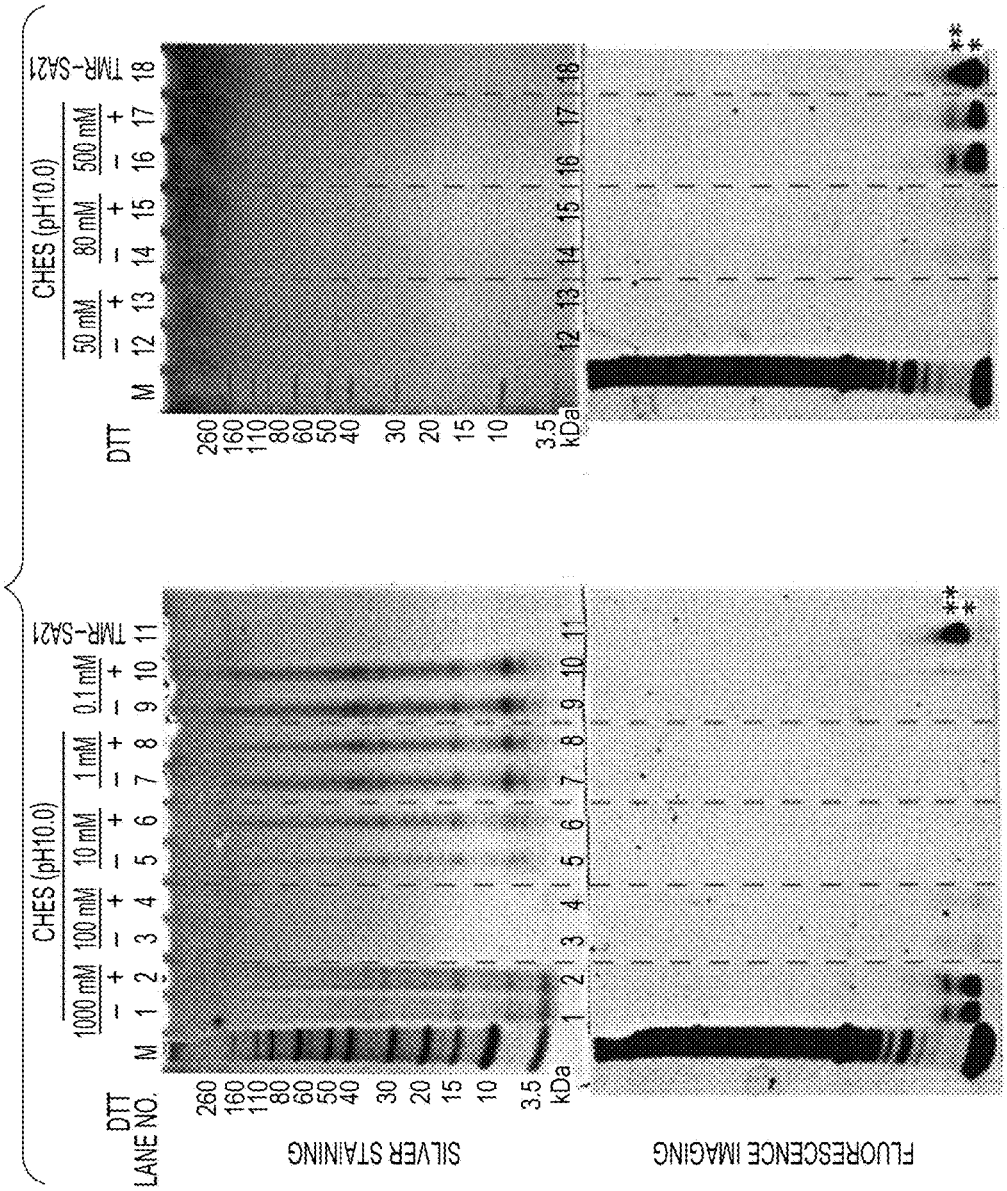
FIG. 4 shows photographs of gels analyzed with fluorescence imaging and silver staining of gels obtained by electrophoresis of samples prepared by homogenizing insoluble fractions with different concentrations of additives (CHES)

The samples were subjected to SDS-PAGE in the same manner as in Example 1, followed by fluorescent imaging and silver staining. FIG. 4 shows the results analyzed by fluorescence imaging and silver staining of gels after electrophoresis. In FIG. 4, the bands of Lane Nos. 11 and 18 of the fluorescence imaged gels (indicated by *) represent bands of TMR-SA21 monomers and the bands (indicated by **) represent bands of TMR-SA21 multimers. Based on the results of fluorescence imaging and silver staining, the relative value of recovery rate (Y), relative value of relative amount of impurities (D), and recovery efficiency were calculated in the same manner as in Example 2. The calculated values are shown in Table 2.

TABLE 2

| Additive | Concentration (mM) | Relative value of recovery rate (Y) | Relative value of relative amount of impurities (D) | Recovery efficiency (Y/D) |
| --- | --- | --- | --- | --- |
| CHES | 1 | 0.01 | 0.89 | 0.01 |
| CHES | 10 | 0.01 | 0.26 | 0.04 |
| CHES | 50 | 0.00 | 0.04 | 0.00 |
| CHES | 80 | 0.02 | 0.04 | 0.56 |
| CHES | 100 | 0.13 ± 0.17 | 0.16 ± 0.25 | 1.18 ± 0.39 |
| CHES | 500 | 0.54 | 0.04 | 15.33 |
| CHES | 1000 | 0.77 | 0.35 | 2.21 |

(3.4) Results

As shown in FIG. 4 and Table 2, it is found that in a case where the CHES concentration is in the range of 0.1 mM to 50 mM, the SA21 peptide is not liberated from the insoluble fraction. As shown in FIG. 4, in a case where the CHES concentration was in the range of 0.1 mM to 50 mM, even further addition of DTT as the reducing agent to the additive caused no liberation of the SA21 peptide from the insoluble fraction. On the other hand, in a case where the CHES concentration is in the range of 80 mM to 1000 mM, the SA21 peptide could be liberated and recovered from the insoluble fraction. Therefore, it was suggested that an appropriate CHES concentration range as the peptide-liberator is from 80 mM to 1000 mM. As shown in FIG. 4, in a case where the CHES concentration was from 80 mM to 1000 mM, even further addition of DTT to the additive allows the SA21 peptide to be efficiently liberated and recovered from the insoluble fraction.

Example 4

Liberation and Recovery of Peptides with CAPSO

It was examined whether it was possible to liberate and recover a peptide incorporated into a self-aggregate of albumin by using additives containing CAPSO (having a structure similar to that of CAPS) with various concentrations. An appropriate CAPSO concentration range as a peptide-liberator was determined.

(4.1) Materials
Additives

The additives used were CAPSO aqueous solutions (pH 10.2) with CAPSO concentrations of 50, 80, 100, 500, and 1000 mM. These CAPSO aqueous solutions were obtained by dissolving 3-(cyclohexylamino)-2-hydroxypropanesulfonic acid (product No. C2278-100G, manufactured by Sigma-Aldrich) so as to have the above concentrations and adjusting the pH to 10.2 using NaOH.

Peptide

The peptide used was the same TMR-SA21 (Biologica) as in Example 2.

Liquid Sample

To diluents of whole blood from healthy individuals, TMR-SA21 was added so as to have a final concentration of 2 μM in the same manner as in Example 2, and liquid samples were prepared.

(4.2) Formation of Self-aggregate of Albumin as Well as Liberation and Recovery of Peptide Each of the liquid samples was heat-treated and cooled in the same manner as in Example 2 to form an insoluble fraction (i.e., a self-aggregate of albumin) in each of the liquid samples. Then, the insoluble fraction was homogenized in the same manner as in Example 2 except that the CAPSO aqueous solution was used as an additive, and supernatants were obtained. The obtained supernatants were stored as samples.

(4.3) Detection of Peptide

Figure 5:
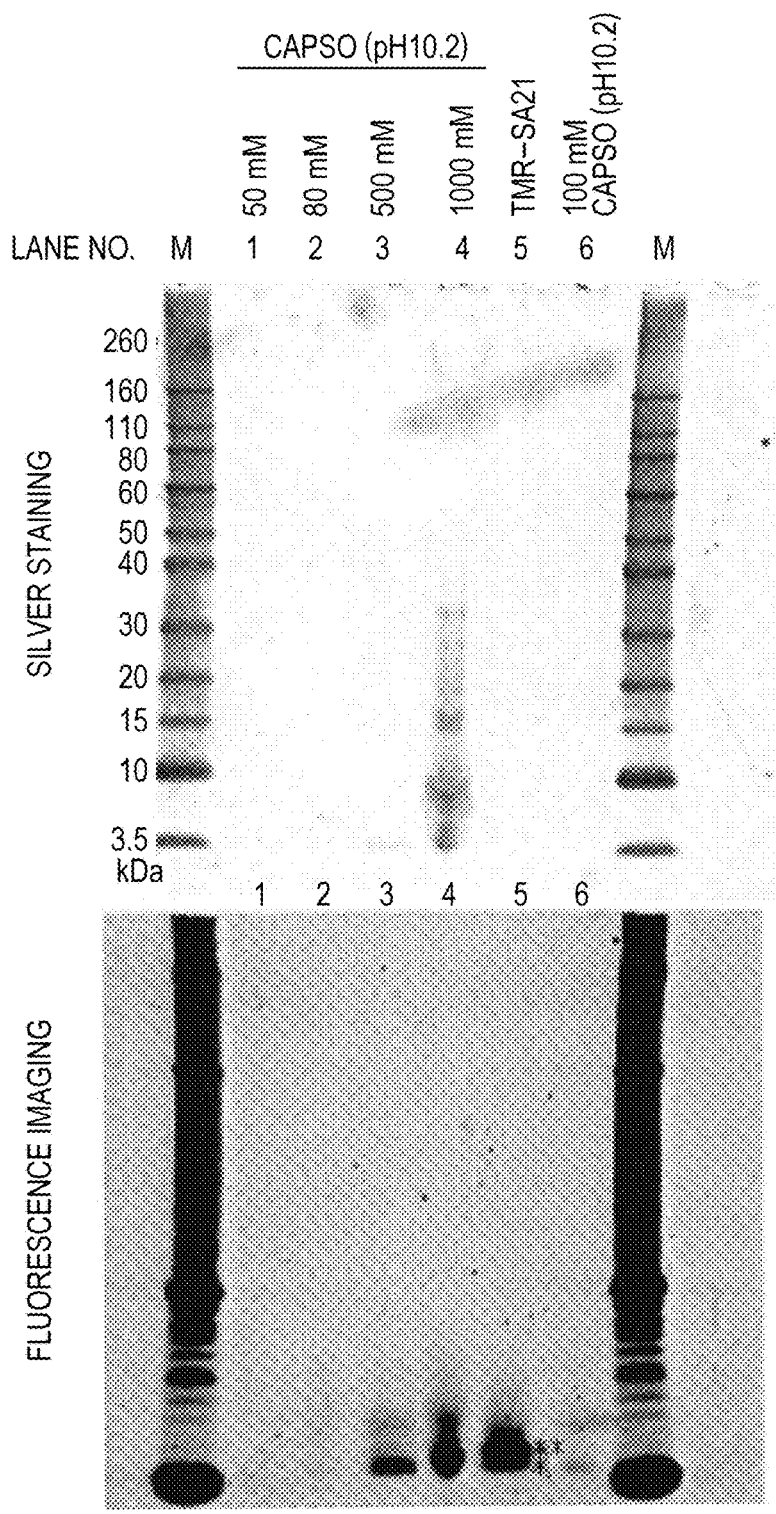
FIG. 5 shows photographs of gels analyzed with fluorescence imaging and silver staining of gels obtained by electrophoresis of samples prepared by homogenizing insoluble fractions with different concentrations of additives (CAPSO)

The samples were subjected to SDS-PAGE in the same manner as in Example 1, followed by fluorescent imaging and silver staining. FIG. 5 shows the results analyzed by fluorescence imaging and silver staining of gels after electrophoresis. In FIG. 5, the band of Lane No. 5 of the fluorescence imaged gel (indicated by *) represents a band of TMR-SA21 monomer and the band (indicated by **) represents a band of TMR-SA21 multimer. Based on the results of fluorescence imaging and silver staining, the relative value of recovery rate (Y), relative value of relative amount of impurities (D), and recovery efficiency were calculated in the same manner as in Example 2. The calculated values are shown in Table 3.

TABLE 3

| Additive | Concentration (mM) | Relative value of recovery rate (Y) | Relative value of relative amount of impurities (D) | Recovery efficiency (Y/D) |
| --- | --- | --- | --- | --- |
| CAPSO | 50 | 0.01 | 0.04 | 0.33 |
| CAPSO | 80 | 0.02 | 0.04 | 0.67 |
| CAPSO | 100 | 0.06 ± 0.03 | 0.02 ± 0.02 | 3.86 ± 3.86 |
| CAPSO | 500 | 0.36 | 0.04 | 10.08 |
| CAPSO | 1000 | 1.34 | 0.47 | 2.87 |

(4.4) Results

As shown in FIG. 5 and Table 3, in a case where the CAPSO concentration was 50 mM, the SA21 peptide was hardly liberated from the insoluble fraction. On the other hand, in a case where the CAPSO concentration was in the range of 80 mM to 1000 mM, the SA21 peptide could be liberated and recovered from the insoluble fraction. Therefore, it was suggested that an appropriate CAPSO concentration range as the peptide-liberator is from 80 mM to 1000 mM.

Example 5

Liberation and Recovery of Peptides with CABS

It was examined whether it was possible to liberate and recover a peptide incorporated into a self-aggregate of albumin by using additives containing CABS (having a structure similar to that of CAPS) with various concentrations. An appropriate CABS concentration range as a peptide-liberator was determined.

(5.1) Materials
Additives

The additives used were CABS aqueous solutions (pH 11.5) with CABS concentrations of 10, 80, 100, 500, and 1000 mM. These CABS aqueous solutions were obtained by dissolving 4-(cyclohexylamino)-1-butanesulfonic acid (product No. C5580-25G, manufactured by Sigma-Aldrich) in water so as to have the above concentrations and adjusting the pH to 11.5 using NaOH.

Peptide

The peptide used was the same TMR-SA21 (Biologica) as in Example 2.

Liquid Sample

To diluents of whole blood from healthy individuals, TMR-SA21 was added so as to have a final concentration of 2 µM in the same manner as in Example 2, and liquid samples were prepared.

(5.2) Formation of Self-aggregate of Albumin as Well as Liberation and Recovery of Peptide Each of the liquid samples was heat-treated and cooled in the same manner as in Example 2 to form an insoluble fraction (i.e., a self-aggregate of albumin) in each of the liquid samples. Then, the insoluble fraction was homogenized in the same manner as in Example 2 except that the CABS aqueous solution was used as an additive, and supernatants were obtained. The obtained supernatants were stored as samples.

(5.3) Detection of Peptide

Figure 6:
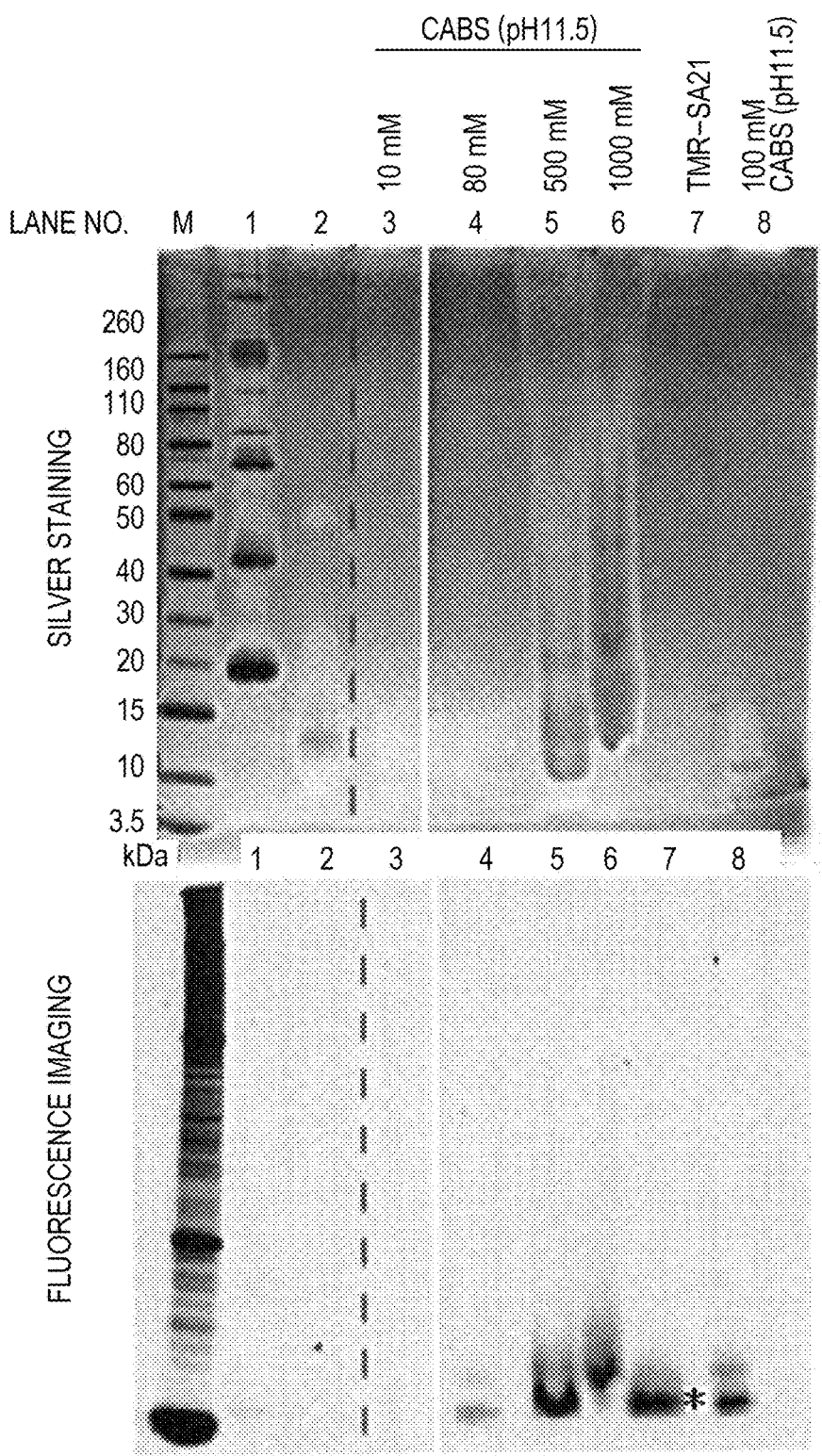
FIG. 6 shows photographs of gels analyzed with fluorescence imaging and silver staining of gels obtained by electrophoresis of samples prepared by homogenizing insoluble fractions with different concentrations of additives (CABS)

The samples were subjected to SDS-PAGE in the same manner as in Example 1, followed by fluorescent imaging and silver staining. FIG. 6 shows the results analyzed by fluorescence imaging and silver staining of gels after electrophoresis. In FIG. 6, the band of Lane No. 7 of the fluorescence imaged gel (indicated by *) represents a band of TMR-SA21. The supernatant obtained by centrifuging the non-heat treated liquid sample was applied to Lane No. 1, whereas the supernatant obtained by heat-treating the liquid sample was applied to Lane No. 2. Based on the results of fluorescence imaging and silver staining, the relative value of recovery rate (Y), relative value of relative amount of impurities (D), and recovery efficiency were calculated in the same manner as in Example 2. The calculated values are shown in Table 4.

TABLE 4

| Additive | Concentration (mM) | Relative value of recovery rate (Y) | Relative value of relative amount of impurities (D) | Recovery efficiency (Y/D) |
| --- | --- | --- | --- | --- |
| CABS | 10 | 0.00 | 0.04 | 0.00 |
| CABS | 80 | 0.17 | 0.04 | 4.84 |
| CABS | 100 | 0.42 ± 0.37 | 0.28 ± 0.32 | 2.08 ± 1.03 |
| CABS | 500 | 1.29 | 0.11 | 11.92 |
| CABS | 1000 | 0.33 | 0.79 | 0.41 |

(5.4) Results

As shown in FIG. 6 and Table 4, in a case where the CABS concentration was 10 mM, the SA21 peptide was not liberated from the insoluble fraction. On the other hand, in a case where the CABS concentration was in the range of 80 mM to 1000 mM, the SA21 peptide could be liberated and recovered from the insoluble fraction. Therefore, it was suggested that the range of appropriate CABS concentration range as the peptide-liberator is from 80 mM to 1000 mM.

Example 6

Type of Liberator (1)

In Example 6, it was examined whether it was possible to liberate and recover a peptide incorporated into a self-aggregate of albumin by using additives containing compounds having a structure different from that of CAPS.

(6.1) Materials
Additives

The additives used were a 100 mM CHAPS aqueous solution (pH 7.6 or 10.8), DW (18 MΩ·cm), TBPB (pH 7.0 or 11.2), a 100 mM ADA aqueous solution (pH 7.4 or 10.5), a 100 mM bicine aqueous solution (pH 9.0 or 10.3), and a 5 mM sodium hydroxide aqueous solution. The controls used were a 100 mM CAPS aqueous solution (pH 11.0) and a 100 mM CHES aqueous solution (pH 10.0). The CHAPS aqueous solution was obtained by dissolving 3-[(3-cholamidopropyl)dimethylammonio]propanesulfonate (product No. C008, manufactured by DOJINDO LABORATORIES) in water so as to have a final concentration of 100 mM and adjusting the pH to 7.6 or 10.8 using NaOH. The ADA aqueous solution was obtained by dissolving N-(2-acetamide) iminodiacetic acid (product No. 349-08281, manufactured by DOJINDO LABORATORIES) in water so as to have a final concentration of 100 mM and adjusting the pH to 7.4 or 10.5 using NaOH. The bicine aqueous solution was obtained by dissolving N,N-bis(2-hydroxyethyl)glycine (product No. 349-08301, manufactured by DOJINDO LABORATORIES) in water so as to have a final concentration of 100 mM and adjusting the pH to 9.0 or 10.3 using NaOH. To each of the additives, DTT was added so as to have a final concentration of 0.1 mM and a DTT-containing additive was prepared.

Peptide

The peptide used was the same TMR-SA21 (Biologica) as in Example 2.

Liquid Sample

To diluents of whole blood from healthy individuals, TMR-SA21 was added so as to have a final concentration of 2 µM in the same manner as in Example 2, and liquid samples were prepared.

(6.2) Formation of Self-aggregate of Albumin as Well as Liberation and Recovery of Peptide Each of the liquid samples was heat-treated and cooled in the same manner as in Example 2 to form an insoluble fraction (i.e., a self-aggregate of albumin) in each of the liquid samples. Then, the insoluble fraction was homogenized in the same manner as in Example 2 except that the additives were used, and supernatants were obtained. The obtained supernatants were stored as samples.

(6.3) Detection of Peptide

Figure 7:
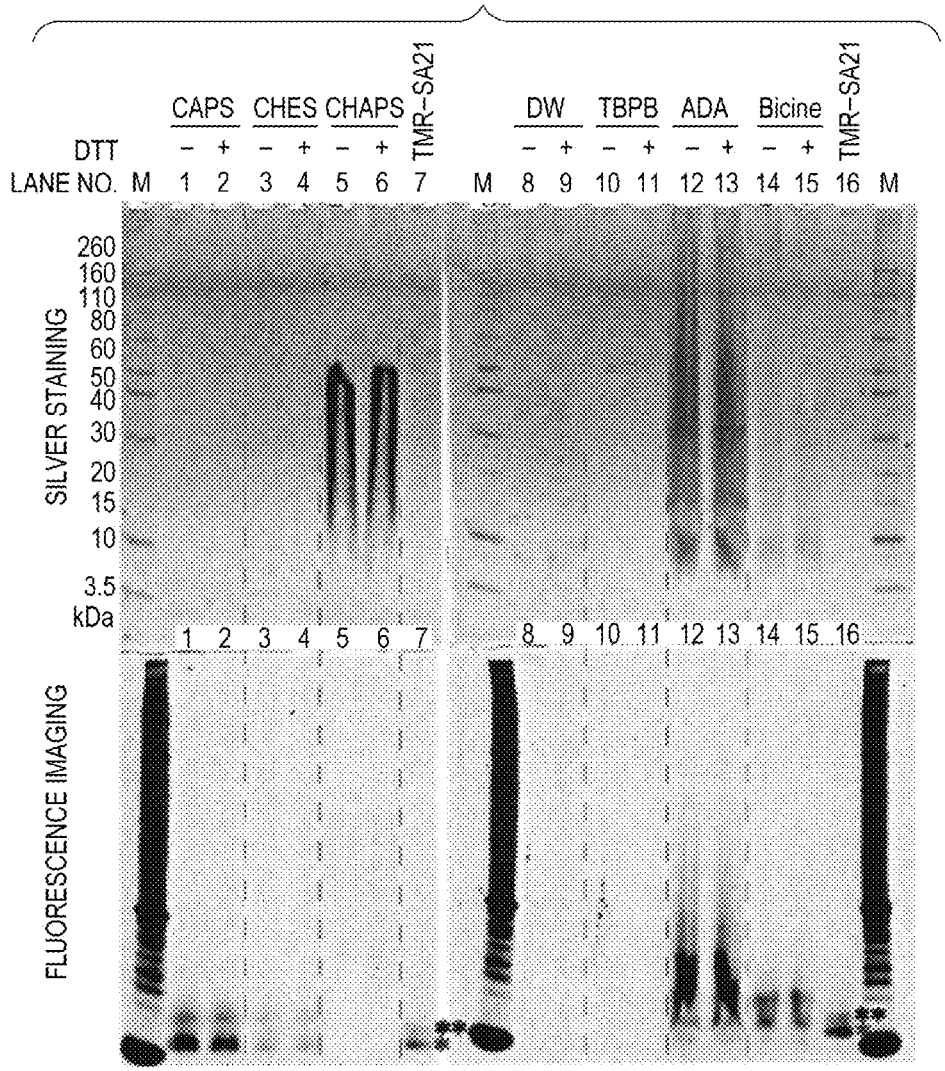
FIG. 7 shows photographs of gels analyzed with fluorescence imaging and silver staining of gels obtained by electrophoresis of samples prepared by homogenizing insoluble fractions with various additives such as bicine.

The samples were subjected to SDS-PAGE in the same manner as in Example 1, followed by fluorescent imaging and silver staining. FIG. 7 shows the results analyzed by fluorescence imaging and silver staining of gels after electrophoresis. FIG. 7 shows photographs of gels obtained by electrophoresis of the samples treated using a 100 mM CHAPS aqueous solution (pH 7.6), DW, TBPB (pH 7.0), a 100 mM ADA aqueous solution (pH 7.4), a 100 mM bicine aqueous solution (pH 9.0), a 100 mM CAPS aqueous solution (pH 11.0), and a 100 mM CHES aqueous solution (pH 10.0). In FIG. 7, the bands of Lane Nos. 7 and 16 of the fluorescence imaged gels (indicated by *) represent bands of TMR-SA21 monomers and the bands (indicated by **) represent bands of TMR-SA21 multimers. Based on the results of fluorescence imaging and silver staining, the relative value of recovery rate (Y), relative value of relative amount of impurities (D), and recovery efficiency were calculated in the same manner as in Example 2. The calculated values are shown in Table 5.

TABLE 5

| Additive | Concentration (mM) | Relative value of recovery rate (Y) | Relative value of relative amount of impurities (D) | Recovery efficiency (Y/D) |
| --- | --- | --- | --- | --- |
| Bicine (pH 9.0) | 100 | 0.23 ± 0.10 | 0.43 ± 0.12 | 0.53 ± 0.09 |
| Bicine (pH 10.3) | 100 | 0.50 | 0.04 | 14.13 |
| CHAPS (pH 7.6) | 100 | 0.00 ± 0.00 | 2.73 ± 2.89 | 0.00 ± 0.00 |
| CHAPS (pH 10.8) | 100 | 0.00 | 4.08 | 0.00 |
| ADA (pH 7.4) | 100 | 0.49 ± 0.17 | 2.35 ± 1.37 | 0.28 ± 0.18 |
| ADA (pH 10.5) | 100 | 0.71 | 5.72 | 0.12 |
| TBPB (pH 7.0) | 100 | 0.00 ± 0.00 | 0.30 ± 0.37 | 0.00 ± 0.00 |
| TBPB (pH 11.2) | 100 | 0.01 | 0.04 | 0.26 |
| DW | — | 0.00 ± 0.00 | 0.27 ± 0.33 | 0.06 ± 0.10 |
| NaOH | 5 | 0.00 | 0.04 | 0.08 |

(6.4) Results

FIG. 7 and Table 5 showed that in a case where CHAPS, TBPB, and DW were used as additives, the SA21 peptide could not be liberated from the insoluble fraction. Even if the sodium hydroxide solution as well as CHAPS and TBPB each with a pH adjusted to 10 or more were used, the SA21 peptide could not be liberated. Thus, it was suggested that the structure of the peptide-liberator is important rather than pH in liberation of the peptide from the insoluble fraction. In the case of using ADA as an additive, the SA21 peptide could be liberated from the insoluble fraction, but a large amount of foreign substances was also liberated. Therefore, the purity of the peptides liberated with the ADA aqueous solution is assumed to be low. On the other hand, in the case of using the bicine aqueous solution as an additive, the SA21 peptide could be liberated and recovered from the insoluble fraction. As the pH of the bicine aqueous solution is higher, foreign substances are hardly liberated and the recovery efficiency of the SA21 peptide is improved. Therefore, it was found that the 100 mM bicine aqueous solution (pH 9.0 or 10.3) can be used as the peptide-liberator for liberation of the peptide incorporated into the self-aggregate of albumin.

Example 7

Type of Liberator (2)

In Example 7, it was examined whether it was possible to liberate and recover a peptide incorporated into a self-aggregate of albumin by using N-cyclohexylsulfamic acid having a structure similar to that of CAPS, and taurine having an amino group and a sulfonic acid group, similarly to CAPS.

(7.1) Materials

Additives

The additives used were a 100 mM N-cyclohexylsulfamic acid aqueous solution (pH 12.5) and a 100 mM taurine aqueous solution (pH 9.5). The controls used were a 100 mM CAPS aqueous solution (pH 11.0) and a 100 mM ADA aqueous solution (pH 7.4). The N-cyclohexylsulfamic acid aqueous solution was obtained by dissolving N-cyclohexylsulfamic acid in water so as to have a final concentration of 100 mM and adjusting the pH to 12.5 using NaOH. The taurine aqueous solution was obtained by dissolving 2-amino ethane sulfamic acid (product No. Al2403, manufactured by Alfa Aesar) in water so as to have a final concentration of 100 mM and adjusting the pH to 9.5 using NaOH.

Peptide

The peptide used was the same TMR-SA21 (Biologica) as in Example 2.

Liquid Sample

To diluents of whole blood from healthy individuals, TMR-SA21 was added so as to have a final concentration of 2 µM in the same manner as in Example 2, and liquid samples were prepared.

(7.2) Formation of Self-aggregate of Albumin as Well as Liberation and Recovery of Peptide Each of the liquid samples was heat-treated and cooled in the same manner as in Example 2 to form an insoluble fraction (i.e., a self-aggregate of albumin) in each of the liquid samples. Then, the insoluble fraction was homogenized in the same manner as in Example 2 except that the additives were used, and supernatants were obtained. The obtained supernatants were stored as samples.

(7.3) Detection of Peptide

Figure 8:
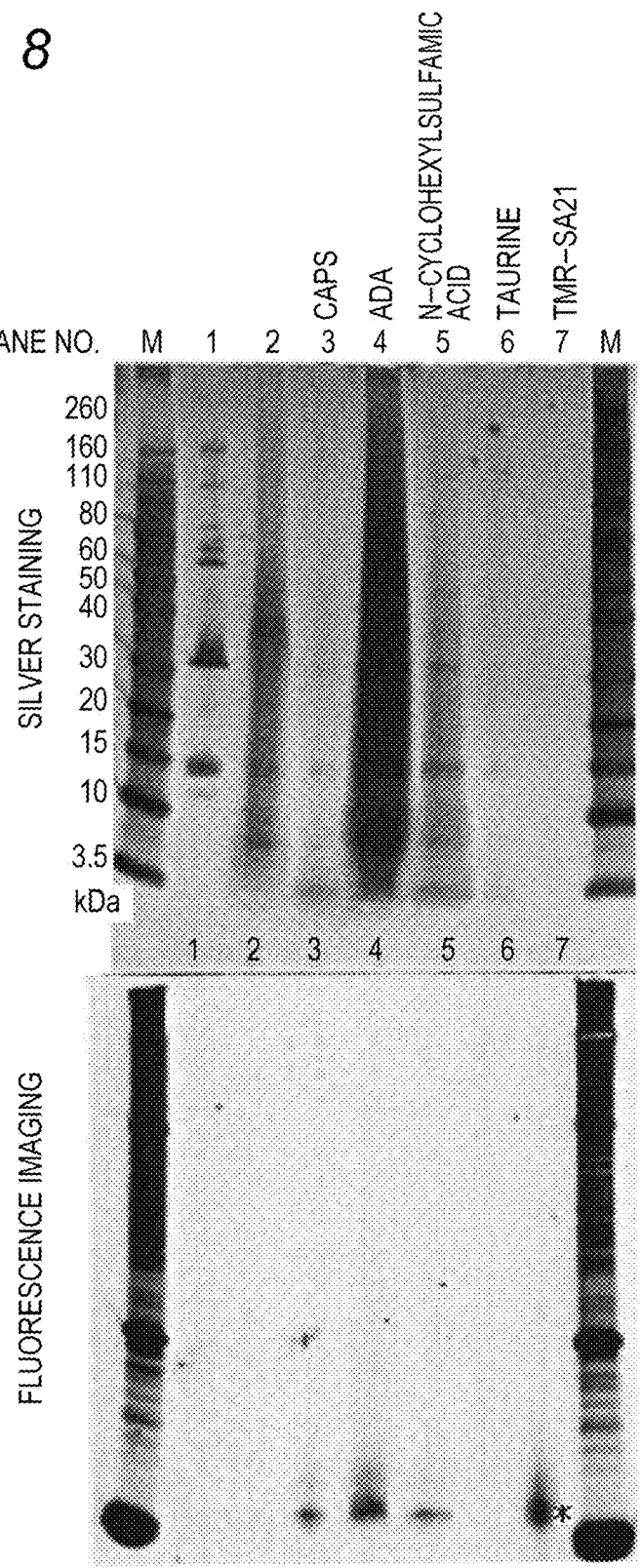
FIG. 8 shows photographs of gels analyzed with fluorescence imaging and silver staining of gels obtained by electrophoresis of samples prepared by homogenizing insoluble fractions with various additives such as N-cyclohexylsulfamic acid.

The samples were subjected to SDS-PAGE in the same manner as in Example 1, followed by fluorescent imaging and silver staining. FIG. 8 shows the results analyzed by fluorescence imaging and silver staining of gels after electrophoresis. In FIG. 8, the band of Lane No. 7 of the fluorescence imaged gel (indicated by *) represents a band of TMR-SA21. The supernatant obtained by centrifuging the non-heat treated liquid sample was applied to Lane No. 1, whereas the supernatant obtained by heat-treating the liquid sample was applied to Lane No. 2. Based on the results of fluorescence imaging and silver staining, the relative value of recovery rate (Y), relative value of relative amount of impurities (D), and recovery efficiency were calculated in the same manner as in Example 2. The calculated values are shown in Table 6.

TABLE 6

| Additive | Concentration (mM) | Relative value of recovery rate (Y) | Relative value of relative amount of impurities (D) | Recovery efficiency (Y/D) |
| --- | --- | --- | --- | --- |
| N-cyclohexylsulfamic acid | 100 | 0.24 | 0.56 | 0.43 |
| Taurine | 100 | 0.00 | 0.05 | 0.00 |

(7.4) Results

FIG. 8 and Table 6 showed that in the case of using taurine as an additive, the SA21 peptide could not be liberated from the insoluble fraction. On the other hand, in the case of using N-cyclohexylsulfamic acid as an additive, the SA21 peptide could be liberated and recovered from the insoluble fraction. Thus, it was found that the 100 mM N-cyclohexylsulfamic acid aqueous solution (pH 12.5) can be used as the peptide-liberator for liberation of the peptide incorporated into the self-aggregate of albumin.

Example 8

Liberation of Peptide without Physical Treatments

In Example 8, the liberation and recovery of a peptide from a self-aggregate were attempted without homogenization in the contact of a self-aggregate of albumin containing a peptide incorporated therein with a peptide-liberator.

(8.1) Materials

Additives

The additives used were a 100 mM CAPS aqueous solution (PH 11.0), a 100 mM ADA aqueous solution (pH 7.4), a 100 mM bicine aqueous solution (pH 9.0), and TBPB (pH 7.0).

Peptide

The peptide used was the same TMR-SA21 (Biologica) as in Example 2.

Liquid Sample

To diluents of whole blood from healthy individuals, TMR-SA21 was added so as to have a final concentration of 2 μM in the same manner as in Example 2, and liquid samples were prepared.

Figure 9A:
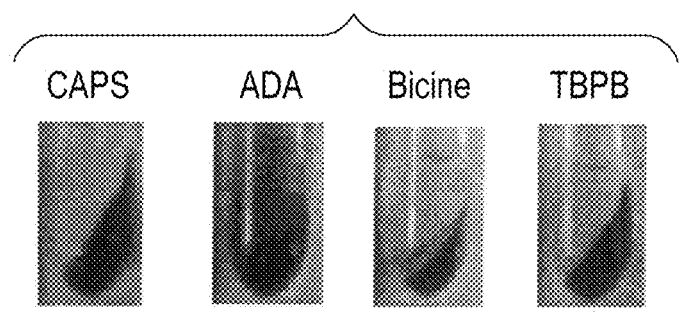
FIG. 9A shows photographs of insoluble fractions obtained by bringing into contact with various additives and leaving the fractions to stand for two days.

(8.2) Formation of Self-aggregate of Albumin as Well as Liberation and Recovery of Peptide Each of the liquid samples was heat-treated and cooled in the same manner as in Example 2 to form an insoluble fraction (i.e., a self-aggregate of albumin) in each of the liquid samples. The insoluble fraction was transferred from each of the liquid samples after heat treatment into a 2-mL volume microtube (manufactured by Eppendorf) using a spatula. The additives were added to the microtube, and were allowed to stand at room temperature for two days. Two days later, the insoluble fraction was subjected to centrifugation at 15,000 rpm for 5 minutes, and the separated precipitates and supernatants were photographed. The photographs are shown in FIG. 9A. Then, the resultant supernatants were stored as samples.

(8.3) Detection of Peptide

Figure 9B:
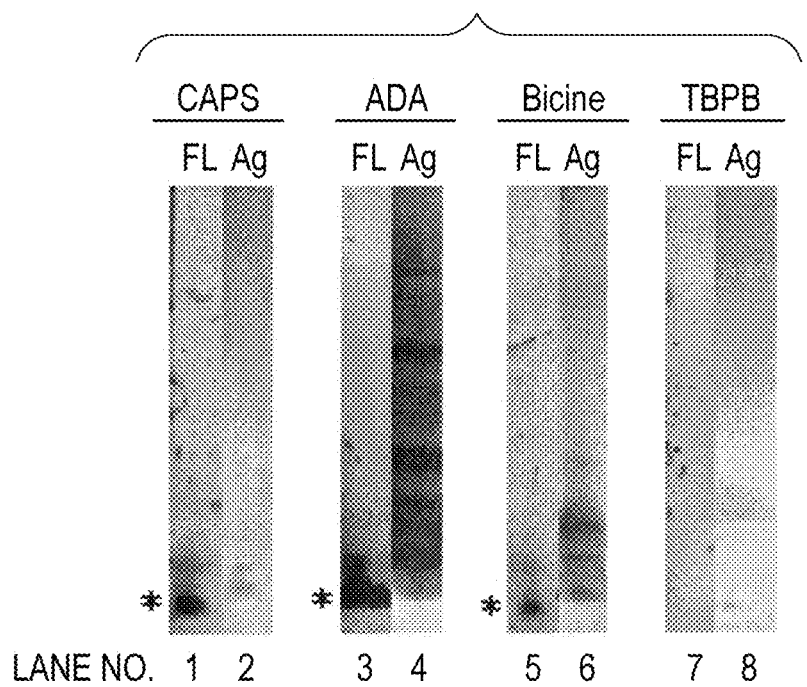
FIG. 9B shows photographs of gels analyzed with fluorescence imaging and silver staining of gels obtained by electrophoresis of samples prepared such that insoluble fractions are brought into contact with various additives and left to stand for two days.

The samples were subjected to SDS-PAGE in the same manner as in Example 1, followed by fluorescent imaging and silver staining. FIG. 9B shows the results analyzed by fluorescence imaging and silver staining of gels after electrophoresis. In FIG. 9B, "FL" represents fluorescence imaging, and "Ag" represents silver staining. The band (indicated by *) represents a band of TMR-SA21.

(8.4) Results

As shown in FIG. 9A, in a case where CAPS, bicine or TBPB was brought into contact with the insoluble fraction, the resultant supernatant was clear. On the other hand, as shown in FIG. 9A, in the case of using ADA, the resultant supernatant was very cloudy. Referring to FIG. 9B, in the case of using CAPS, the SA21 was liberated in the supernatant, and foreign substances were hardly observed (refer to Lane Nos. 1 and 2). In the case of using ADA, the SA21 was liberated in the supernatant and a large amount of foreign substances was also included (refer to Lane Nos. 3 and 4). In the case of using bicine, the SA21 was liberated in the supernatant and a small amount of foreign substances was also observed (refer to Lane Nos. 5 and 6). In the case of using TBPB, neither the SA21 nor foreign substances were observed in the supernatant (refer to Lane Nos. 7 and 8). These facts showed that in the case of using CAPS or bicine as a peptide-liberator, the peptide can be liberated from the self-aggregate of albumin even without using physical treatments such as homogenization and stirring. On the other hand, it was shown that, TBPB cannot liberate the SA21 peptide from the insoluble fraction, whereas ADA dissolves the insoluble fraction.

What is claimed is:

1. A method of liberating a peptide, comprising bringing a self-aggregate of albumin comprising a peptide incorporated therein into contact with a solution that comprises a compound selected from the group consisting of 3-(cyclohexylamino)-1-propanesulfonic acid (CAPS), 2-(cyclohexylamino)ethanesulfonic acid (CHES), 3-(cyclohexylamino)-2-hydroxypropanesulfonic acid (CAPSO), 4-(cyclohexylamino)-1-butanesulfonic acid (CABS), N-cyclohexylsulfamic acid and the compound of Formula (II), the concentration of the compound being 80 mM to 1000 mM in the solution, and allowing the peptide to be liberated from the self-aggregate of albumin into the solution:

[Formula II]

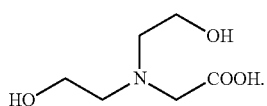

(II)

2. The method according to claim 1, wherein the self-aggregate of albumin is formed by heat-treating a liquid sample containing a complex of peptide and albumin.

3. The method according to claim 1, wherein the compound is CAPS or CHES.

4. The method according to claim 1, wherein the peptide incorporated into the self-aggregate of albumin is liberated into the solution by stirring the self-aggregate of albumin and a solution comprising the compound.

5. The method according to claim 1, wherein the peptide incorporated into the self-aggregate of albumin is a peptide comprising a cysteine residue or is an acidic peptide.

6. The method according to claim 1, wherein the peptide incorporated into the self-aggregate is a peptide present in a biological sample collected from a living body.

7. The method according to claim 6, wherein the biological sample collected from the living body is blood, plasma or serum.

8. The method according to claim 1, wherein the peptide incorporated into the self-aggregate comprises a biomarker present in blood.

9. A method of recovering a peptide, comprising:
bringing a self-aggregate of albumin comprising a peptide incorporated therein into contact with a solution that comprises a compound selected from the group consisting of 3-(cyclohexylamino)-1-propanesulfonic acid (CAPS), 2-(cyclohexylamino)ethanesulfonic acid (CHES), 3-(cyclohexylamino)-2-hydroxypropanesulfonic acid (CAPSO), 4-(cyclohexylamino)-1-butanesulfonic acid (CABS), N-cyclohexylsulfamic acid and the compound of Formula (II), the concentration of the compound being 80 mM to 1000 mM in the solution, and allowing the peptide to be liberated from the self-aggregate of albumin into the solution; and recovering the peptide liberated in the solution:

[Formula II]

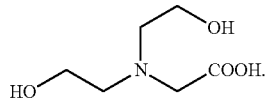

(II)

10. The method according to claim 9, wherein the self-aggregate of albumin is formed by heat-treating a liquid sample containing a complex of peptide and albumin.

11. The method according to claim 9, wherein the compound is CAPS or CHES.

12. The method according to claim 9, wherein the peptide incorporated into the self-aggregate of albumin is liberated into the solution by stirring the self-aggregate of albumin and a solution comprising the compound.

13. The method according to claim 9, wherein the peptide incorporated into the self-aggregate of albumin is a peptide comprising a cysteine residue or is an acidic peptide.

14. The method according to claim 9, wherein the peptide incorporated into the self-aggregate is a peptide present in a biological sample collected from a living body.

15. The method according to claim 14, wherein the biological sample collected from the living body is blood, plasma or serum.

16. The method according to claim 9, wherein the peptide incorporated into the self-aggregate comprises a biomarker present in blood.

17. A method of recovering a peptide, comprising the steps of:

heat-treating a liquid sample containing a complex of peptides and albumin to obtain a supernatant and an insoluble self-aggregate of albumin, the supernatant comprising a first peptide which is liberated from the complex, the self-aggregate of albumin comprising a second peptide;

recovering the supernatant comprising the first peptide;

bringing the self-aggregate of albumin formed by the heat treatment into contact with a solution comprising a compound selected from the group consisting of 3-(cyclohexylamino)-1-propanesulfonic acid (CAPS), 2-(cyclohexylamino)ethanesulfonic acid (CHES), 3-(cyclohexylamino)-2-hydroxypropanesulfonic acid (CAPSO), 4-(cyclohexylamino)-1-butanesulfonic acid (CABS), N-cyclohexylsulfamic acid and the compound of Formula (II), the concentration of the compound being 80 mM to 1000 mM in the solution, so as to allow the second peptide incorporated into the self-aggregate of albumin to be liberated into the solution; and recovering the solution comprising the second peptide liberated from the self-aggregate of albumin:

[Formula II]

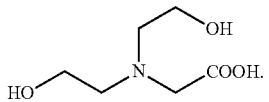

(II)

18. The method according to claim 17, wherein the second peptide is a peptide comprising a cysteine residue or is an acidic peptide.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Homo sapiens

<400> SEQUENCE: 1

Cys Tyr Ile Gln Asn Cys Pro Leu Gly
1               5

<210> SEQ ID NO 2
<211> LENGTH: 31
<212> TYPE: PRT
<213> ORGANISM: Homo sapiens

<400> SEQUENCE: 2

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 3
<211> LENGTH: 18
<212> TYPE: PRT
<213> ORGANISM: Homo sapiens

<400> SEQUENCE: 3

Asp Asp Glu Trp Leu Cys Gly Trp Arg Pro Leu Cys Ile Asp Glu Ile
1               5                   10                  15

Leu Arg
```